(12) United States Patent
Csida et al.

(10) Patent No.: US 11,554,054 B2
(45) Date of Patent: Jan. 17, 2023

(54) ABSORBENT ARTICLE WITH A FASTENING SYSTEM WITH REDUCED WASTE AND METHOD OF MANUFACTURING THE SAME

(71) Applicant: Kimberly-Clark Worldwide, Inc., Neenah, WI (US)

(72) Inventors: Jason Gene Csida, Appleton, WI (US); Rebecca Suzanne Walter, Hortonville, WI (US); Patrick Robert Lord, Appleton, WI (US); Kyle Mark Barriger, Neenah, WI (US); Eric-John Raoul Gilgenbach, Winneconne, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 139 days.

(21) Appl. No.: 16/893,520

(22) Filed: Jun. 5, 2020

(65) Prior Publication Data
US 2020/0297546 A1    Sep. 24, 2020

Related U.S. Application Data

(62) Division of application No. 15/117,652, filed as application No. PCT/US2014/032220 on Mar. 28, 2014, now Pat. No. 10,709,615.

(51) Int. Cl.
*A61F 13/56*    (2006.01)
*A61F 13/58*    (2006.01)
(Continued)

(52) U.S. Cl.
CPC .. *A61F 13/15756* (2013.01); *A61F 13/15772* (2013.01); *A61F 13/5633* (2013.01);
(Continued)

(58) Field of Classification Search
CPC ....................................................... A61F 13/58
See application file for complete search history.

(56) References Cited

U.S. PATENT DOCUMENTS 3,598,114 A * 8/1971 Lewis .................. A61F 13/148
602/19
4,522,874 A * 6/1985 Pommez ........... A61F 13/15252
428/351
(Continued)

FOREIGN PATENT DOCUMENTS

CN        1937931 A    3/2007
EP       0379850 A1    8/1990
(Continued)

*Primary Examiner* — Catharine L Anderson
*Assistant Examiner* — Arjuna P Chatrathi
(74) *Attorney, Agent, or Firm* — Kimberly-Clark Worldwide, Inc.

(57) ABSTRACT

An absorbent article with a fastening system with reduced waste and method of manufacturing such an absorbent article is disclosed. The method of manufacturing an absorbent article can include cutting a first web of ear tab material to provide a first ear tab that is registered and cutting a second web of ear tab material to provide a second ear tab that is registered. The method can also include providing a web of ear panel material, coupling the first and second ear tabs to the web of ear panel material, cutting the web of ear panel material to provide first and second ear panels to form first and second ears, and coupling the first and second ears to the absorbent assembly to form at least a portion of the fastening system for the absorbent article. The first and second ears can be configured to be different from one another.

18 Claims, 15 Drawing Sheets

(51) Int. Cl.
  *A61F 13/62* (2006.01)
  *A61F 13/15* (2006.01)
  *B29C 65/48* (2006.01)
  *B29C 65/56* (2006.01)
  *B29L 31/48* (2006.01)

(52) U.S. Cl.
  CPC ............ *A61F 13/58* (2013.01); *A61F 13/622* (2013.01); *B29C 65/48* (2013.01); *B29C 65/56* (2013.01); *A61F 2013/587* (2013.01); *B29L 2031/4878* (2013.01)

(56) References Cited

U.S. PATENT DOCUMENTS

| | | | |
|---|---|---|---|
| 5,110,386 A | 5/1992 | Ochi et al. | |
| 5,312,387 A | 5/1994 | Rossini et al. | |
| 5,401,275 A * | 3/1995 | Flug | A61F 13/622 |
| | | | 604/389 |
| 5,580,411 A | 12/1996 | Nease et al. | |
| 5,603,708 A | 2/1997 | Seth | |
| 5,705,013 A | 1/1998 | Nease et al. | |
| 5,759,317 A | 6/1998 | Justmann | |
| 5,876,531 A | 3/1999 | Jacobs et al. | |
| 6,195,850 B1 | 3/2001 | Melbye et al. | |
| 6,200,299 B1 | 3/2001 | Heki | |
| 6,264,784 B1 | 7/2001 | Menard et al. | |
| 6,572,598 B1 | 6/2003 | Ashton et al. | |
| 6,730,189 B1 | 5/2004 | Franzmann et al. | |
| 6,743,324 B2 | 6/2004 | Hargett et al. | |
| 6,746,435 B1 | 6/2004 | Van Tilburg | |
| 7,214,285 B2 | 5/2007 | Guenther et al. | |
| 7,371,302 B2 | 5/2008 | Miyamoto et al. | |
| 7,407,496 B2 | 8/2008 | Petersen | |
| 7,534,481 B2 | 5/2009 | Seth et al. | |
| 7,578,811 B2 | 8/2009 | Corneliusson | |
| 7,658,813 B2 | 2/2010 | Petersen | |
| 7,867,212 B2 | 1/2011 | Waksmundzki et al. | |
| 7,871,400 B2 | 1/2011 | Sablone et al. | |
| 7,901,534 B2 | 3/2011 | Gaston et al. | |
| 7,918,961 B2 | 4/2011 | Wada et al. | |
| 8,016,972 B2 | 9/2011 | Andrews et al. | |
| 8,067,063 B2 | 11/2011 | Desai et al. | |
| 8,092,630 B2 * | 1/2012 | Ikegami | A01K 23/00 |
| | | | 156/259 |
| 8,096,981 B2 | 1/2012 | Putzer et al. | |
| 8,097,298 B2 | 1/2012 | Piantoni et al. | |
| 8,172,977 B2 | 5/2012 | McCabe et al. | |
| 8,357,135 B2 | 1/2013 | de Dier et al. | |
| 2010/0192739 A1 | 8/2010 | Piantoni et al. | |
| 2011/0046597 A1* | 2/2011 | Mizutani | A61F 13/622 |
| | | | 604/385.25 |
| 2011/0208144 A1* | 8/2011 | Roe | A61F 13/49014 |
| | | | 604/366 |
| 2012/0190523 A1 | 7/2012 | Pastrello et al. | |

FOREIGN PATENT DOCUMENTS

| | | |
|---|---|---|
| EP | 0233704 B1 | 7/1992 |
| EP | 1208823 A1 | 5/2002 |
| EP | 1539074 B1 | 3/2006 |
| EP | 1663095 B1 | 10/2008 |
| EP | 2238955 B1 | 12/2011 |
| EP | 2586411 B1 | 8/2014 |
| WO | 04069093 A2 | 8/2004 |
| WO | 12052134 A1 | 4/2012 |
| WO | 12100823 A1 | 8/2012 |

* cited by examiner

ABSORBENT ARTICLE WITH A FASTENING SYSTEM WITH REDUCED WASTE AND METHOD OF MANUFACTURING THE SAME

RELATED APPLICATIONS

The present application is a divisional application and claims priority to U.S. patent application Ser. No. 15/117,652, filed on Aug. 9, 2016, which is a national-phase entry, under 35 U.S.C. § 371, of PCT Patent Application No. PCT/US14/32220, filed on Mar. 28, 2014, all of which are incorporated herein by reference.

BACKGROUND

Disposable absorbent articles are often provided with a fastening system that can retain the absorbent article in a wear configuration on the wearer. These fastening systems often include two pairs of complementary fastener components. As an example, diapers often include a hook fastener component on each rear ear which can engage a loop fastener component located in a front waist region of the diaper. Of course, other fastening means can be used as an alternative or in combination with a hook/loop fastening components. In some circumstances, the rear ears include an ear panel and an ear tab coupled to the ear panel. The ear tab can include the hook fastener component, or other fastening means. These fastening systems, particularly the rear ears, can be formed in a variety of methods. Many of the methods of forming the rear ears involve waste of material, from the ear panel materials, the tab materials, or both.

One method of manufacturing the rear ears for an absorbent article includes coupling the ear tab material, and fastener component thereon, to the ear panel material. Then the rear ears may be cut from the composite material in the shape of the rear ears, and then applied to the chassis of the diaper. An example of this method is described in U.S. Pat. No. 7,371,302 issued to Myamoto et al. Although this method can cut the rear ears in a nested configuration that provides no waste of trim material, the tab material is cut at the same pitch as the ear panel material, and as a result, may be larger than necessary which may lead to unnecessary amounts of the tab material and fastening component thereon. Additionally, having the same pitch between the ear tab material and the ear panel material limits the potential options in shape of the ear.

Another method of manufacturing the rear ears of an absorbent article can include separately cutting the ear panel material from the ear tab material, such as described in U.S. Pat. No. 7,871,400 issued to Sablone et al. and U.S. Patent Application Publication No. 2012/0190523 by Pastrello et al. While the manufacturing methods disclosed therein provide for cutting the ear panels in a nested configuration to reduce waste, the configuration of the rear ear panels and the ear tab materials coupled thereto are mostly linear in shape, including corners that in some circumstances can provide irritation or discomfort to the wearer and may be less appealing to the wearer or user as the simple shape may tend to portray the appearance of a lower-tiered product. These manufacturing methods also do not provide an ability to vary the location of the fastening forces of the rear ears based on the shape of the ear tab, which may limit the fastening and fit properties of the absorbent article.

Thus, there remains a need for a method of manufacturing an absorbent article with a fastening system having reduced waste yet can overcome at least one or more of the disadvantages discussed above.

SUMMARY

In one embodiment, a method of manufacturing an absorbent article with a fastening system with reduced waste is provided. The absorbent article can include an absorbent assembly including an outer cover, a bodyside liner, and an absorbent body disposed between the outer cover and the bodyside liner. The method can include providing a first web of ear tab material and a second web of ear tab material. The method can further include cutting the first web of ear tab material to provide a first ear tab. The first ear tab can be cut in such a manner that the first ear tab is registered. The method can also include cutting the second web of ear tab material to provide a second ear tab. The second ear tab can be cut in such a manner that the second ear tab is registered. The method can include providing a web of ear panel material and coupling the first ear tab and the second ear tab to the web of ear panel material. Additionally, the method can include cutting the web of ear panel material to provide a first ear panel and a second ear panel. The first ear tab can be coupled to the first ear panel to form a first ear and the second ear tab can be coupled to the second ear panel to form a second ear. The method can also include coupling the first ear and the second ear to the absorbent assembly to form at least a portion of the fastening system for the absorbent article.

In another embodiment, a method of manufacturing an absorbent article with a fastening system with reduced waste is provided. The absorbent article can include an absorbent assembly including an outer cover, a bodyside liner, and an absorbent body disposed between the outer cover and the bodyside liner. The method can include providing a primary web of ear tab material and cutting the primary web of ear tab material in a non-linear fashion to provide a first web of ear tab material and a second web of ear tab material. The method can further include phasing the first web of ear tab material to cut the first web of ear tab material to provide a first ear tab that is registered and phasing the second web of ear tab material to cut the second web of ear tab material to provide a second ear tab that is registered. Furthermore, the method can include providing a web of ear panel material and coupling the first ear tab and the second ear tab to the web of ear panel material. The method can also include cutting the web of ear panel material to provide a first ear panel and a second ear panel. The first ear tab can be coupled to the first ear panel to form a first ear and the second ear tab can be coupled to the second ear panel to form a second ear. Additionally, the method can include coupling the first ear and the second ear to the absorbent assembly to form at least a portion of the fastening system for the absorbent article.

In another embodiment, an absorbent article can include an absorbent assembly that includes an outer cover, a bodyside liner, and an absorbent body disposed between the outer cover and the bodyside liner. The absorbent article can also include a fastening system coupled to the absorbent assembly. The fastening system can include a first rear ear including a first ear tab with a fastening component and a second rear ear including a second ear tab with a fastening component. A majority of the fastening component of the first ear tab can be above a latitudinal axis of the first rear ear and a majority of the fastening component of the second ear tab can be below a latitudinal axis of the second rear ear.

BRIEF DESCRIPTION OF THE DRAWINGS

A full and enabling disclosure thereof, directed to one of ordinary skill in the art, is set forth more particularly in the remainder of the specification, which makes reference to the appended figures in which.

DETAILED DESCRIPTION

The present disclosure is generally directed towards methods of manufacturing an absorbent article with a fastening system having reduced waste that overcomes at least some of the deficiencies noted above. It should be appreciated that the term "absorbent article" used herein refers to an article which may be placed against or in proximity to the body (i.e., contiguous with the body) of the wearer to absorb and contain various liquid, solid, and semi-solid exudates discharged from the body. While such absorbent articles are often intended to be discarded after a limited period of use instead of being laundered or otherwise restored for reuse, the present disclosure is not limited to such disposable articles, and instead, applies to both disposable and reusable absorbent articles.

It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure. Additionally, while the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross-direction manufacturing of a product, without departing from the spirit and scope of the disclosure.

The exemplary methods and absorbent articles that are presented are provided by way of explanation and are not meant as limitations. For example, features illustrated or described as part of one embodiment or figure can be used on another embodiment or figure to yield yet another embodiment. It is intended that the present disclosure include such modifications and variations. These features will become more apparent with reference to the accompanying drawings.

Figure 1:
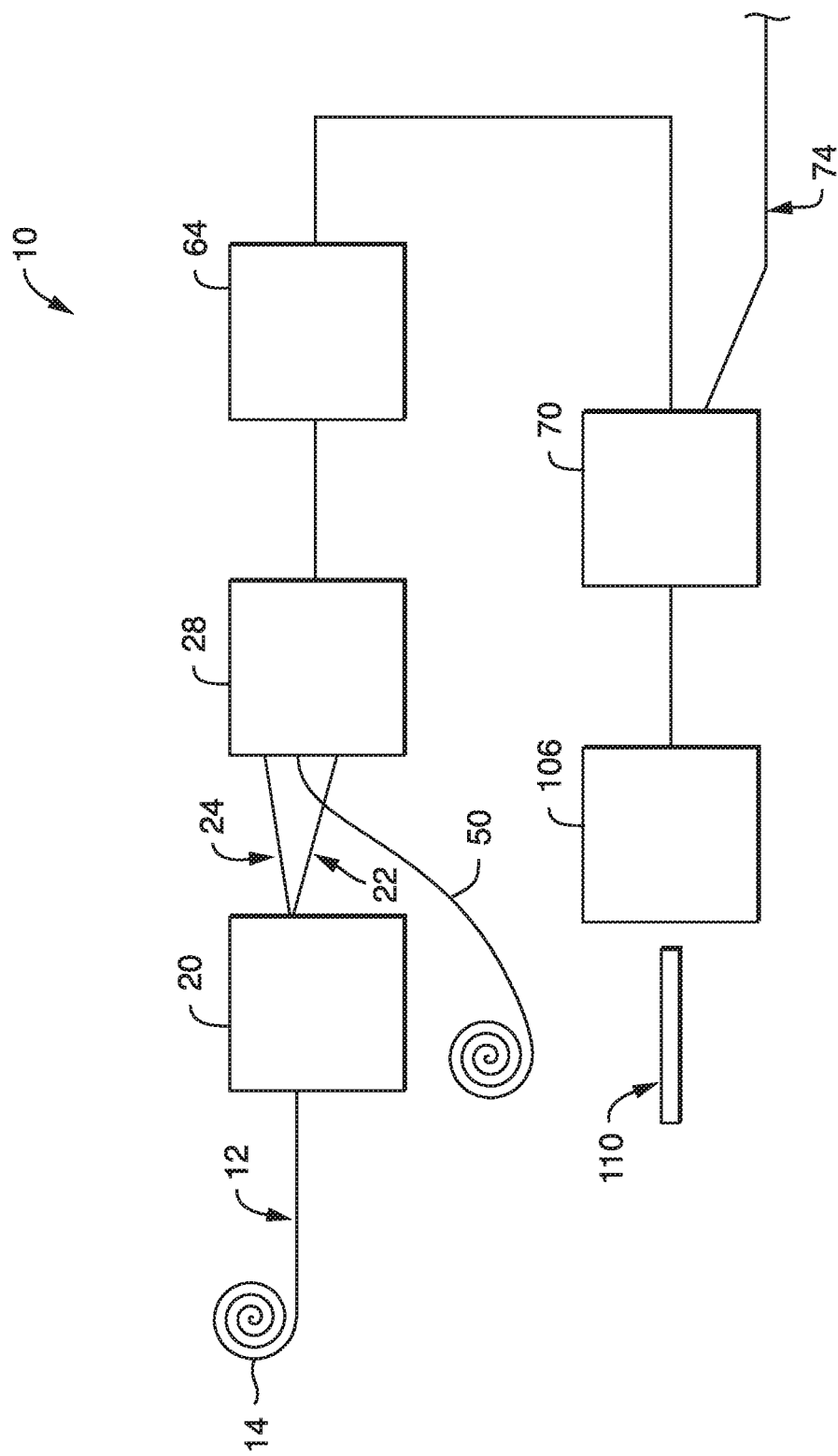
FIG. 1 is a process diagram showing an exemplary method of manufacturing an absorbent article according to the invention.
Figure 2:
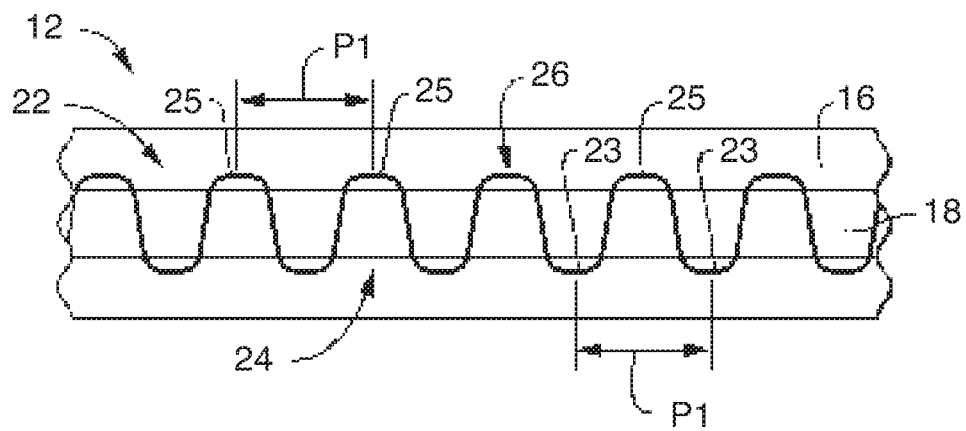
FIG. 2 is a top view of a primary web of ear tab material after being cut by the cutting module in the method of FIG. 1.

Referring to FIG. 1, a method 10 of manufacturing an absorbent article 110 with a fastening system with reduced waste is depicted. The method 10 can include providing a primary web of ear tab material 12. The primary web of ear tab material 12 can be on a roll 14. In one embodiment, the primary web of ear tab material 12 can include a base material 16 and a fastening component 18 (as shown in FIG. 2). In one embodiment, the base material 16 can be a spunbond-meltblown-spunbond ("SMS") material, however, the base material 16 can be composed of other materials. In the embodiment described herein, the fastening component 18 includes a hook material. However, the fastening component could alternatively or additionally include other fastening components including, but not limited to, loop materials, adhesives, cohesives, snaps, etc. The fastening component 18 can be configured in one longitudinal lane such as shown in FIG. 2, multiple longitudinal lanes, or in any other suitable configuration.

The primary web of ear tab material 12 can be transferred to a cutting module 20 where it can be longitudinally cut into a first web of ear tab material 22 and a second web of ear tab material 24 in a non-linear fashion. In the embodiment described herein, the cutting module 20 can longitudinally cut the primary web of ear tab material 12 into the first web of ear tab material 22 and the second web of ear tab material 24 as shown in FIG. 2, where a repeated, sinusoidal-type cut 26 is made in the primary web of ear tab material 12. The cut 26 can pass through the fastening component 18 on the primary web of ear tab material 12. Of course, it is intended that other types of cuts can be made into the primary web of ear tab material 12 to provide a first web of ear tab material 22 and a second web of ear tab material 24. The cutting module 20 can perform the cut 26 with equipment known to those of ordinary skill in the art such that the cut 26 has a pitch P1. As illustrated in FIG. 2, pitch P1 can be the distance between adjacent projections 23 on the first web of ear tab material 22, which is also the distance between adjacent projections 25 on the second web of ear tab material 24. As further shown in FIG. 2, cutting the primary web of ear tab material 12 along cut 26 can provide a nested ear tab pattern with no trim waste being formed when providing the first web of ear tab material 22 and the second web of ear tab material 24 from the primary web of ear tab material 12. It is to be noted that while the cutting module 20 is shown as being an in-line process in the method 10 of manufacturing the absorbent article 110, this step could be provided as an off-line process, and thus, an off-line process of cutting the primary web of ear tab material 12 is intended to be within the scope of this disclosure.

Figure 3:
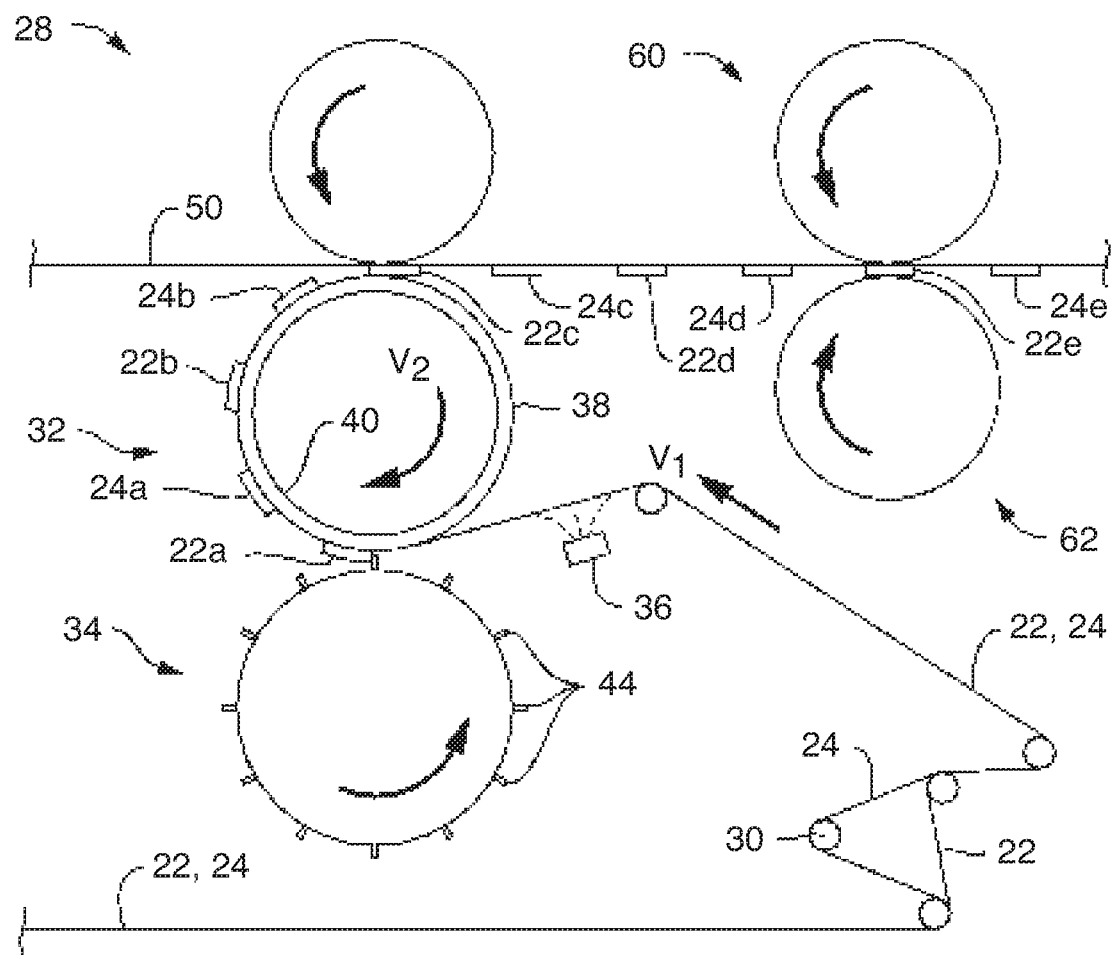
FIG. 3 is a side view of the tab applicator module of the method of FIG. 1.

After exiting the cutting module 20, the first and second webs of ear tab material 22, 24, respectively, can be separated from one another and transferred on web paths of different lengths to the tab applicator module 28. As shown in FIG. 3, this can be accomplished by traversing the second web of ear tab material 24 around an idler 30 that the first web of ear tab material 22 does not traverse. The difference in length of the web paths of the first and second webs of ear tab material 22, 24 prior to entering the tab applicator module 28 can change the phasing between cross-directionally adjacent projections 23, 25 on the first and the second webs of ear tab material 22, 24, respectively, as compared to the phasing between cross-directionally adjacent projections 23, 25 at the point of cutting the primary web of ear tab material 12 by the cutting module 20 (as shown in FIG. 2). This change in phasing between the first and second webs of ear tab material 22, 24 can assist with the proper machine direction placement of individual ear tabs on the web of ear panel material 50 in the tab applicator module 28 that will be explained further below. To help with this, the idler 30 can be moveable to compensate and adjust the phasing of the second web of ear tab material 24 with respect to the first web of ear tab material 22 as necessary.

The first web of ear tab material 22 and the second web of ear tab material 24 can also cross one another in a cross-direction fashion after the cutting module 20 and prior to the tab applicator module 28, as shown in FIG. 1, such that the projections 23, 25 of the first and second webs of ear tab material 22, 24 along cut 26 face away from one another to be in a proper orientation for downstream processing. The web paths of the first and second webs of ear tab material 22, 24 can also provide for the proper cross-directional separation and alignment for individual ear tabs to be cut from the first and second webs of ear tab material 22, 24 and be coupled to the web of ear panel material 50, as will be discussed further below.

As briefly mentioned above and as shown in FIGS. 1 and 3, the method 10 can also include a tab applicator module 28. The tab applicator module 28 can include an anvil roll 32 and a knife roll 34. As shown in FIG. 3, adhesive can be applied to the first web of ear tab material 22 and the second web of ear tab material 24 by adhesive station 36 prior to the first and second webs of ear tab material 22, 24 being transferred to the anvil roll 32. Adhesive station 36 can apply adhesive to the first and second webs of ear tab material 22, 24 by a spray, a slot-coat, a pulsed application, or any other method deemed suitable.

Figure 4:
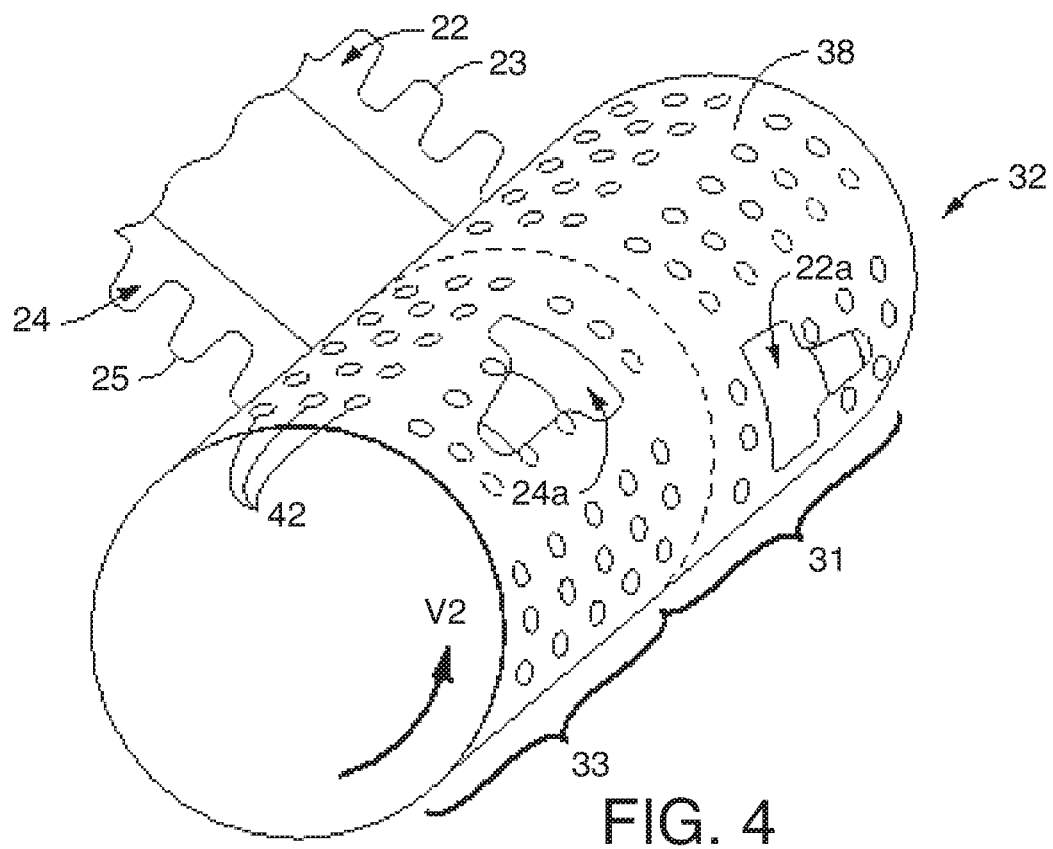
FIG. 4 is a perspective view of an anvil roll of the tab applicator module of FIG. 3.

As depicted in FIGS. 3 and 4, the anvil roll 32 can be a vacuum roll and can include an outer surface 38 and an inner surface 40. A plurality of vacuum holes 42 can be formed in the outer surface 38 of the anvil roll 32 and can be in fluid contact with the inner surface 38 of the anvil roll 32. The anvil roll 32 may internally contain or otherwise be connected to a suitable vacuum source (such as, e.g., a vacuum pump, a vacuum chamber, etc., not shown) which is capable of selectively applying vacuum pressure (i.e., negative pressure) through the one or more vacuum holes 42 such that materials located on the outer surface 38 of the anvil roll 32 are generally drawn to and secured against the outer surface 38. In some embodiments, the vacuum source may be capable of applying a vacuum in the range of 1 to 30 inches of water.

In the illustrated embodiment herein, the first and second webs of ear tab material 22, 24 are fed to the anvil roll 32 at a slower linear speed (as indicated by V1 in FIG. 3) than the surface speed of the anvil roll 32 (as indicated by V2 in FIG. 3). In other words, the surface speed of the anvil roll 32 is greater than the speed at which the incoming first and second webs of ear tab material 22, 24 are fed to the anvil roll 32. As a result, the leading edges of incoming first and second webs of ear tab material 22, 24 engage and slip against the outer surface 38 of the anvil roll 32. It is understood that the incoming first and second webs of ear tab material 22, 24 can be fed to the anvil roll 32 at any suitable rate. As illustrated in FIG. 4, the anvil roll 32 can be configured to have two circumferential zones 31, 33 of vacuum holes 42. The first web of ear tab material 22 can be fed into the anvil roll 32 in alignment with one circumferential zone 31 of vacuum holes, while the second web of ear tab material 24 can be fed into the anvil roll 32 in alignment with the other circumferential zone 33 of vacuum holes 42. Of course, the vacuum holes 42 can be configured in a variety of suitable ways, including in a consistent pattern across the entire outer surface 38 of the anvil roll 32 such that there are not distinct circumferential zones 31, 33.

Figure 5:
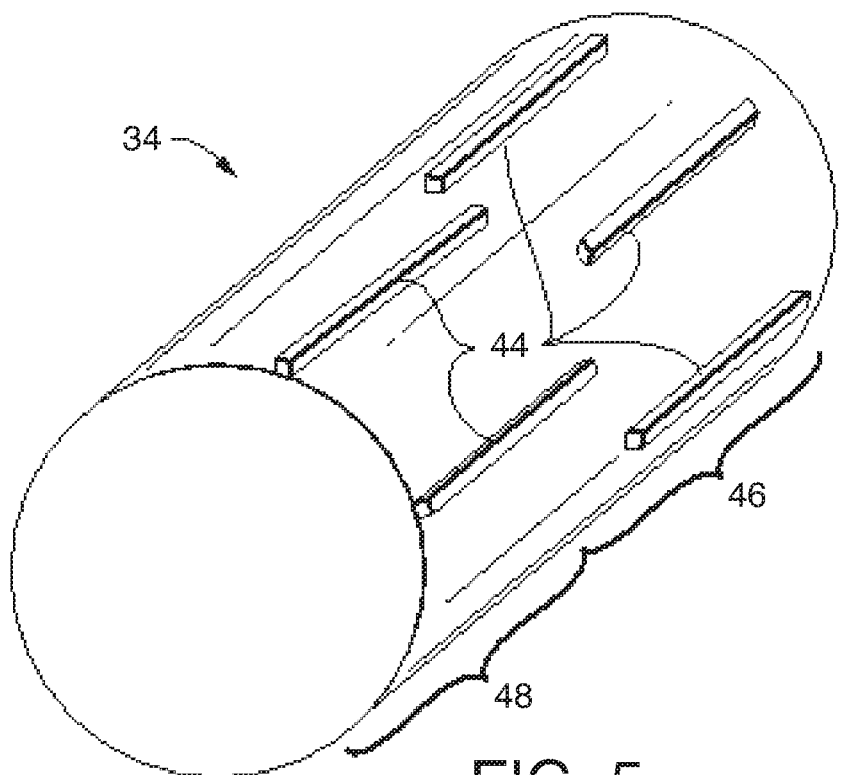
FIG. 5 is a perspective view of a knife roll of the tab applicator module of FIG. 3.

To cut the first and second webs of ear tab material 22, 24, the method 10 can include a knife roll 34. In the embodiment described herein, the knife roll 34 can include twelve knife edges 44. The knife edges 44 can be configured to cut material provided on the outer surface 38 of the anvil roll 32 when the knife edges 44 come into contact with the outer surface 38 of the anvil roll 32, such as with anvils (not shown) fixed to the outer surface 38 of the anvil roll 32. In the embodiment illustrated in FIGS. 3 and 5, when the first and second webs of ear tab material 22, 24 are fed to the anvil roll 32, the knife edges 44 will cut the first and second webs of ear tab material 22, 24 in a transverse or cross-machine direction when the knife edges 44 come into contact with the outer surface 38 of the anvil roll 32, thereby forming individual ear tabs. For example, FIG. 3 depicts ear tabs 22a, 22b, 22c, 22d, and 22e being cut from the first web of ear tab material 22 and individual ear tabs 24a, 24b, 24c, 24d, and 24e being cut from the second web of ear tab material 24. As shown in FIG. 5, the knife edges 44 can be configured to be in circumferential zones 46, 48, with knife edges 44 being offset between circumferential zones 46, 48 to account for the offset in phasing between the first web of ear tab material 22 and the second web of ear tab material 24, as will be discussed in more detail below. One of the circumferential zones 46, 48 can be configured to be on an operator side of the tab applicator module 28 and the other zone can be configured to be on a drive side of the tab applicator module 28. The circumferential zones 46, 48 on the knife roll 34 can correspond to the circumferential zones 31, 33 on the anvil roll 32.

Figure 6A:
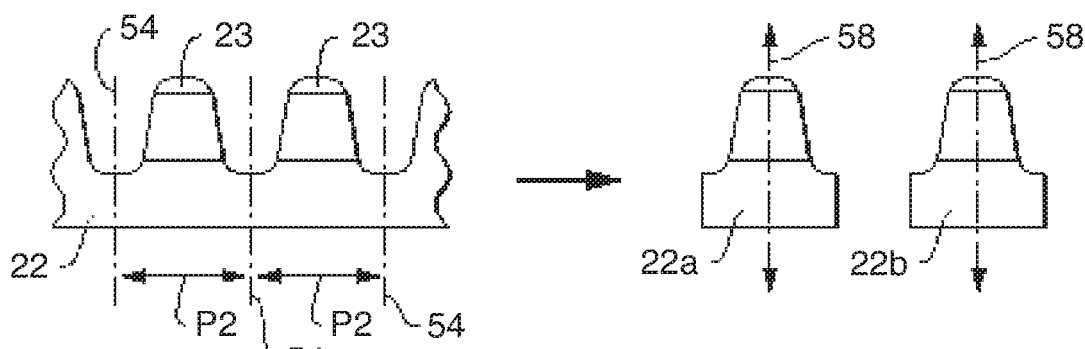
FIG. 6A is a top view of symmetric, registered ear tabs being cut from a first web of ear tab material by the tab applicator module of FIG. 3.
Figure 6B:
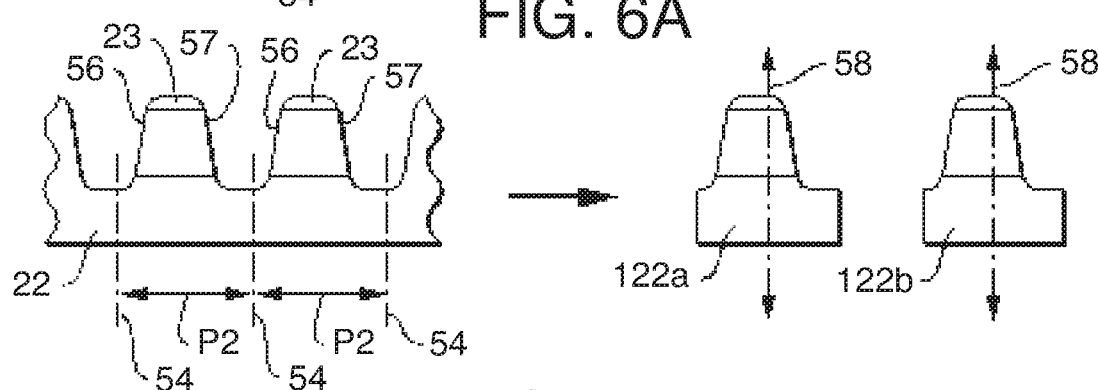
FIG. 6B is a top view of asymmetric, registered ear tabs being cut from a first web of ear tab material by the tab applicator module of FIG. 3.
Figure 6C:
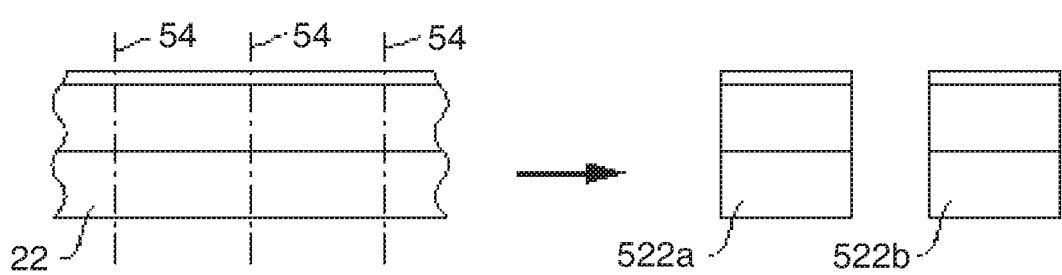
FIG. 6C is a top view of a non-registered ear tab being cut from a first web of ear tab material as is known in the prior art.
Figure 6D:
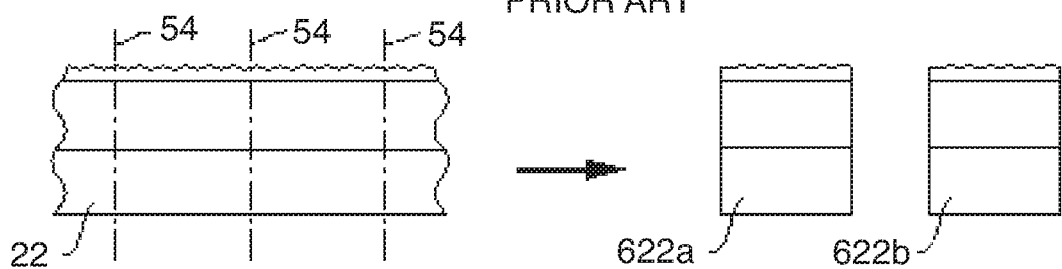
FIG. 6D is a top view of an alternative non-registered ear tab being cut from a first web of ear tab material as is known in the prior art.

The first and second webs of ear tab material 22, 24 are each cut in such a manner to provide registered ear tabs. FIGS. 6A and 6B provide two examples of the first web of ear tab material 22 being cut to provide registered ear tabs 22a, 22b (FIG. 6A) and 122a, 122b (FIG. 6B). Of course, although the illustrated embodiments in FIGS. 6A and 6B provide examples of cutting the first web of ear tab material 22 to provide registered ear tabs, the same process is applicable to the second web of ear tab material 24. As used herein, the term "registered ear tabs" means that the webs of ear tab material 22, 24 are configured in such a manner and the knife roll 34 is configured in such a manner that the webs of ear tab material 22, 24 are cut to produce ear tabs not only at a repeated, specific pitch, but also with initial phasing with respect to the webs of ear tab material 22, 24 that provides a meaningful difference in the resultant shape of the ear tabs that are formed from the webs of ear tab material 22, 24. In contrast, "non-registered ear tabs," examples of which are shown by ear tabs 522a and 522b in FIG. 6C and ear tabs 622a and 622b in FIG. 6D and are known in the prior art, can be formed by cutting a web of ear tab material 22 at cuts 54 with a repeated, specific pitch, however, the initial phasing of the cuts 54 to the web of ear tab material 22 does not provide any meaningful difference to the resultant shape of the ear tabs 522a, 522b, 622a, and 622b.

FIG. 6A depicts an embodiment in which the knife roll 34 was phased with respect to the first web of ear tab material 22 to provide symmetric, registered ear tabs 22a, 22b. As shown in FIG. 6A, three cuts 54 are made in the first web of ear tab material 22 at a pitch P2, with each cut 54 being in a position equidistant between successive projections 23 of the first web of ear tab material 22. This phasing of cuts 54 provides registered ear tabs 22a, 22b that are symmetric about a latitudinal axis 58 of the ear tabs 22a, 22b and provides that ear tab 22a is identical to ear tab 22b. The pitch P2 as illustrated in FIG. 6A can be equal to the pitch P1 as shown in FIG. 2.

FIG. 6B depicts an embodiment in which the knife roll 34 was phased with respect to the first web of ear tab material 22 to provide asymmetric, registered ear tabs 122a, 122b. As shown in FIG. 6B, three cuts 54 are made in the first web of ear tab material 22 at a pitch P2, with each cut 54 being in a position that is not equidistant between successive projections 23 of the first web of ear tab material 22. In other words, the cuts 54 are made in the first web of ear tab material 22 at a position that is closer to one projection 23 in comparison to the next successive projection 23. More specifically, in the embodiment illustrated in FIG. 6A, each cut 54 is placed closer to the upstream side 56 of each projection 23 than to the downstream side 57 of the next successive projection 23. This phasing of the cuts 54 to the first web of ear tab material 22 provides registered ear tabs 122a, 122b that are asymmetric about a latitudinal axis 58 of the ear tabs 122a, 122b and provides that ear tab 122a is identical to ear tab 122b. It is to be noted that the cuts 54 could be provided with a different phasing with respect to the first web of ear tab material 22 and provide other embodiments of asymmetric, registered ear tabs. As but one example, each cut 54 could be provided in the first web of ear tab material 22 to be closer to the downstream side 57 of each projection 23 than to the upstream side 56 of the next successive projection 23. As noted above with respect to FIG. 6A, the pitch P2 as illustrated in FIG. 6B can be equal to the pitch P1 as illustrated in FIG. 2.

Figure 6E:
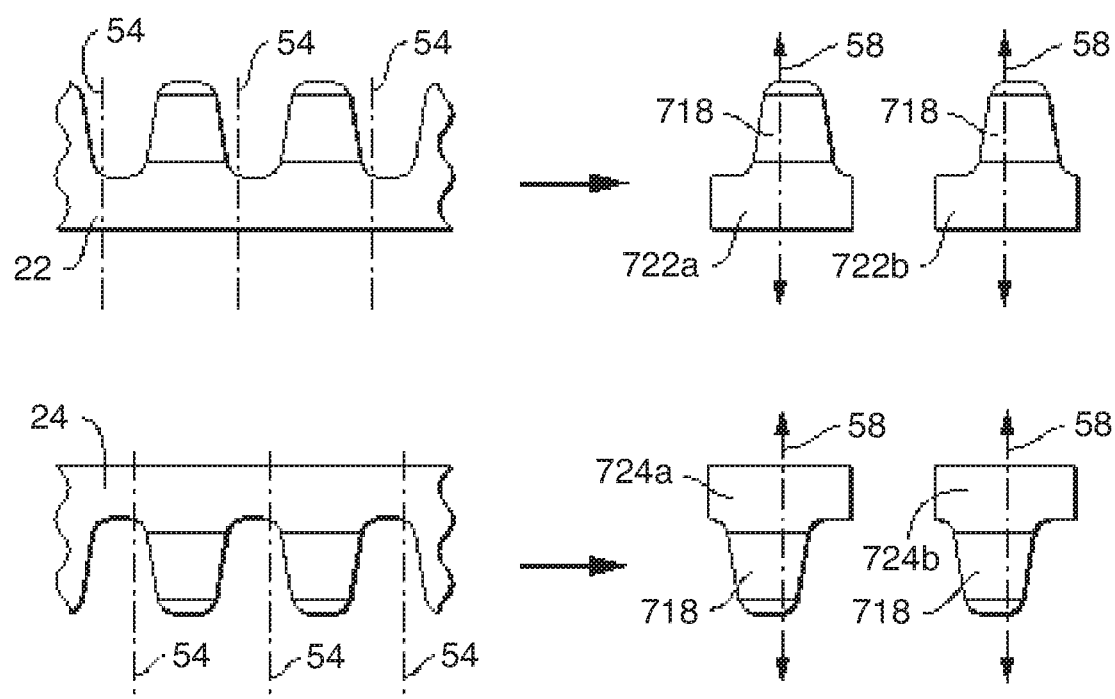
FIG. 6E is a top view of first and second webs of ear tab material being phased and cut to provide ear tabs that differ between the first and the second webs of ear tab material.

Although in some embodiments the first web of ear tab material 22 and the second web of ear tab material 24 can be phased with respect to one another and cut to provide individual ear tabs that are the same or mirror-images of one another, in other embodiments the first web of ear tab material 22 can be phased with respect to one another and cut to provide individual ear tabs from the first web of ear tab material 22 that are different in shape than the individual ear tabs from the second web of ear tab material 24. FIG. 6E provides an exemplary embodiment where the phasing and cutting of the first web of ear tab material 22 provides asymmetric ear tabs 722a and 722b and the phasing and cutting of the second web of ear tab material 24 provides asymmetric ear tabs 724a and 724b that differ from ear tabs 722a and 722b. The ear tabs 722a and 722b from the first web of ear tab material 12 have more fastening component 718 (such as hook material) on the right side of the latitudinal axis 58 than on the left side of latitudinal axis 58 and the ear tabs 724a and 724b have more fastening component 718 on the left side of the latitudinal axis 58 than on the right side of latitudinal axis 58.

In some embodiments, such as those shown in FIGS. 6A-6C and 6E, the first and second webs of ear tab material 22, 24 can be cut to form ear tabs such that no waste is formed from the first web of ear tab material 22 and the second web of ear tab material 24.

Figure 7:
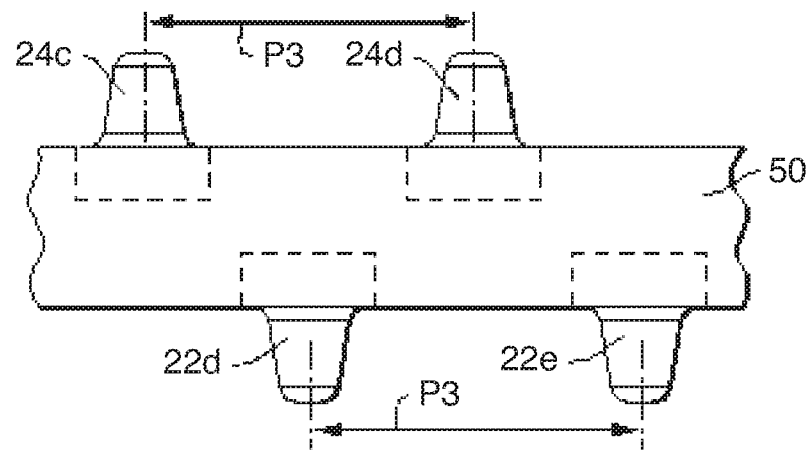
FIG. 7 is a top view of ear tabs coupled to a web of ear panel material in the tab applicator module of FIG. 3.

Once the first and second webs of ear tab material 22, 24 have been cut by the knife edges 44, the individual ear tabs formed will be transported at the surface speed of the anvil roll 32 and be coupled to a web of ear panel material 50, as shown in FIGS. 3 and 7. The web of ear panel material 50 can be an elastic composite material, such as a necked bonded laminate ("NBL"), however, the web of ear panel material 50 could be other elastic materials, other stretchable but inelastic materials, or non-stretchable materials. The ear tabs (such as ear tabs 22a and 24a shown in FIG. 4) are held to the outer surface 38 of the anvil roll 32 by the vacuum drawn through the vacuum holes 42 in the anvil roll 32. The ear tabs 22a and 24a will travel at the same surface speed as the anvil roll 32 until they reach the web of ear panel material 50, where they can be coupled to the web of ear panel material 50. In the embodiment depicted in FIG. 3, the ear tabs are coupled to the ear panel material 50 by passing through a nip defined by the anvil roll 32 and a stomper roll 52, which helps the adhesive on the ear tabs (which was applied to the first and second webs of ear tab material 22, 24 by adhesive station 36) couple the ear tabs to the web of ear panel material 50. FIG. 7 illustrates an embodiment of how the ear tabs 22d, 22e, 24c, and 24d can be coupled to the web of ear panel material 50. Due to the difference in speeds V2 and V1 between the anvil roll 38 and the difference in phasing between the first and second webs of ear tab material 22, 24, the pitch P3 between adjacent ear tabs 22d and 22e or 24c and 24d in FIG. 7 on the web of ear panel material 50 can be greater than the pitch P2 (the distance between adjacent projections 23 or adjacent projections 25 on the first and second webs of ear tab material 22, 24, respectively, and the distance between successive cuts 54 to form the individual ear tabs from the first and second webs of ear tab material 22, 24). This difference between pitches P2 and P3 provides for proper spacing of the ear tabs 22d, 22e, 24c and 24d on the web of ear panel material 50 to provide for cutting of the ear panels to form ears, as will be discussed further below.

As shown in FIG. 3, a pressure bonding horn 60 and a pressure bonding anvil roll 62 can also be provided to increase the bond strength between the individual ear tabs to the web of ear panel material 50. The pressure bonding horn 60 and pressure bonding anvil roll 62 can provide a continuous or an intermittent pressure bond between the individual ear tabs and the web of ear panel material 50. While adhesives and a pressure bond are described as one technique to bond the ear tabs to the web of ear panel material 50, it is contemplated that in other embodiments, the individual ear tabs can be coupled to the web of ear panel material 50 using other suitable bonding techniques, including, but not limited to, the use of adhesives alone, or adhesives used along with ultrasonic bonding.

Figure 8:
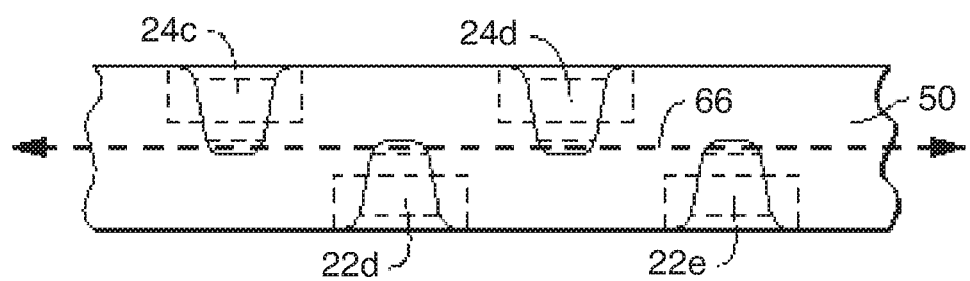
FIG. 8 is a top view of ear tabs coupled to a web of ear panel material and folded upon the web of ear panel material by the folding module of the method of FIG. 1.

After the ear tabs are coupled to the web of ear panel material 50, the ear tabs and the web of ear panel material 50 can then be transported downstream for further processing in method 10. For example, in one embodiment, the method 10 can include a folding module 64. The web of ear panel material 50 and ear tabs can be transported to a folding module 64, which can fold the ear tabs towards a longitudinal axis 66 of the web of ear panel material 50. For example, FIG. 8 illustrates one embodiment of ear tabs 22d, 22e, 24c, and 24d folded towards the longitudinal axis 66 of the web of ear panel material 50 and folded upon the web of ear panel material 50.

Figure 9A:
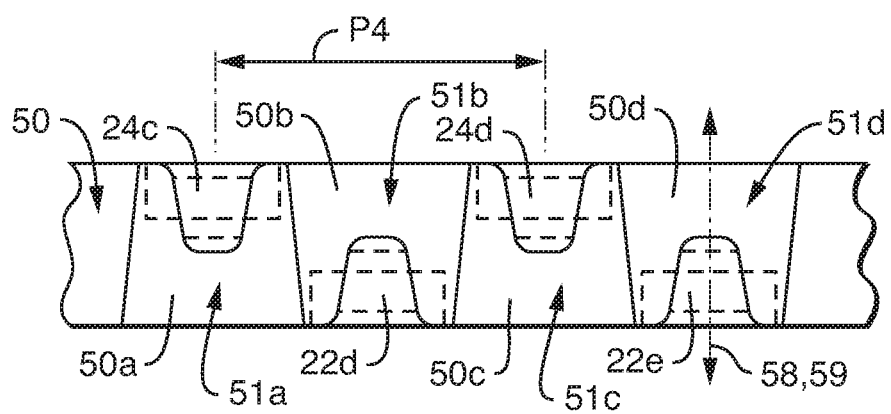
FIG. 9A is a top view of a web of ear panel material being cut into trapezoidal ear panels by an ear cut-and-place module of the method of FIG. 1.
Figure 9B:
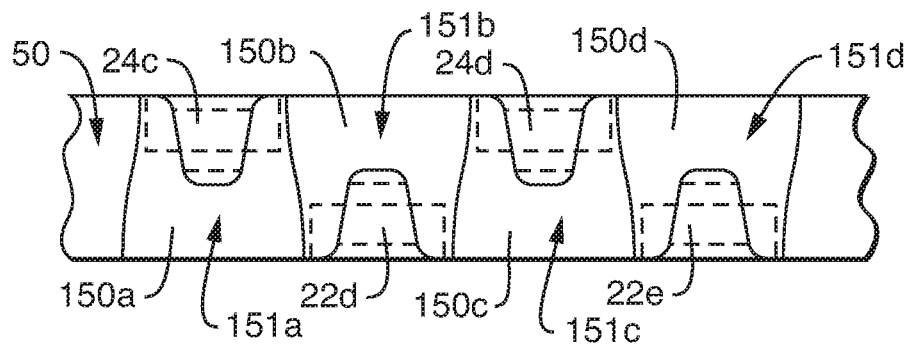
FIG. 9B is a top view of a web of ear panel material being cut into ear panels of an alternative shape by an ear cut-and-place module of the method of FIG. 1.

Method 10 can also include an ear cut-and-place module 70, as shown in FIG. 1. The ear cut-and-place module 70 can provide the functions of cutting the web of ear panel material 50 to form individual ear panels and coupling the ear panels to an absorbent assembly 72. In one embodiment, the ear cut-and-place module 70 can cut the web of ear panel material 50 to form trapezoidal shaped ear panels 50a, 50b, 50c, and 50d as shown in FIG. 9A. Alternatively, the ear cut-and-place module 70 can cut the web of ear panel material 50 to form ear panels 150a, 150b, 150c, and 150d that have at least one non-linear side, or two non-linear sides, as shown in FIG. 9B. In some embodiments, the ear cut-and-place module 70 can cut individual ear panels from the web of ear panel material 50 and form no waste from the web of ear panel material. The ear cut-and-place module 70 can cut the web of ear panel material 50 to form ear panels at a pitch P4, the distance between successive ear panels (e.g., 50a, 50c) of the same orientation, as illustrated in FIG. 9A. The pitch P4 can be equal to the pitch P3, the distance between successive ear tabs of the same orientation (such as ear tabs 24c and 24d), such as shown in FIG. 7. As shown in FIG. 9A, the ear cut-and-place module 70 can also cut the web of ear panel material 50 such that the latitudinal axis 58 of the ear tab (e.g., ear tab 22e) is co-linear with the latitudinal axis 59 of the respective ear panel (e.g., ear panel 51d). In other embodiments, the ear cut-and-place module 70 can cut the web of ear panel material 50 such that the latitudinal axis 58 of the ear tab is not co-linear with the latitudinal axis 59 of the respective ear panel.

Figure 10:
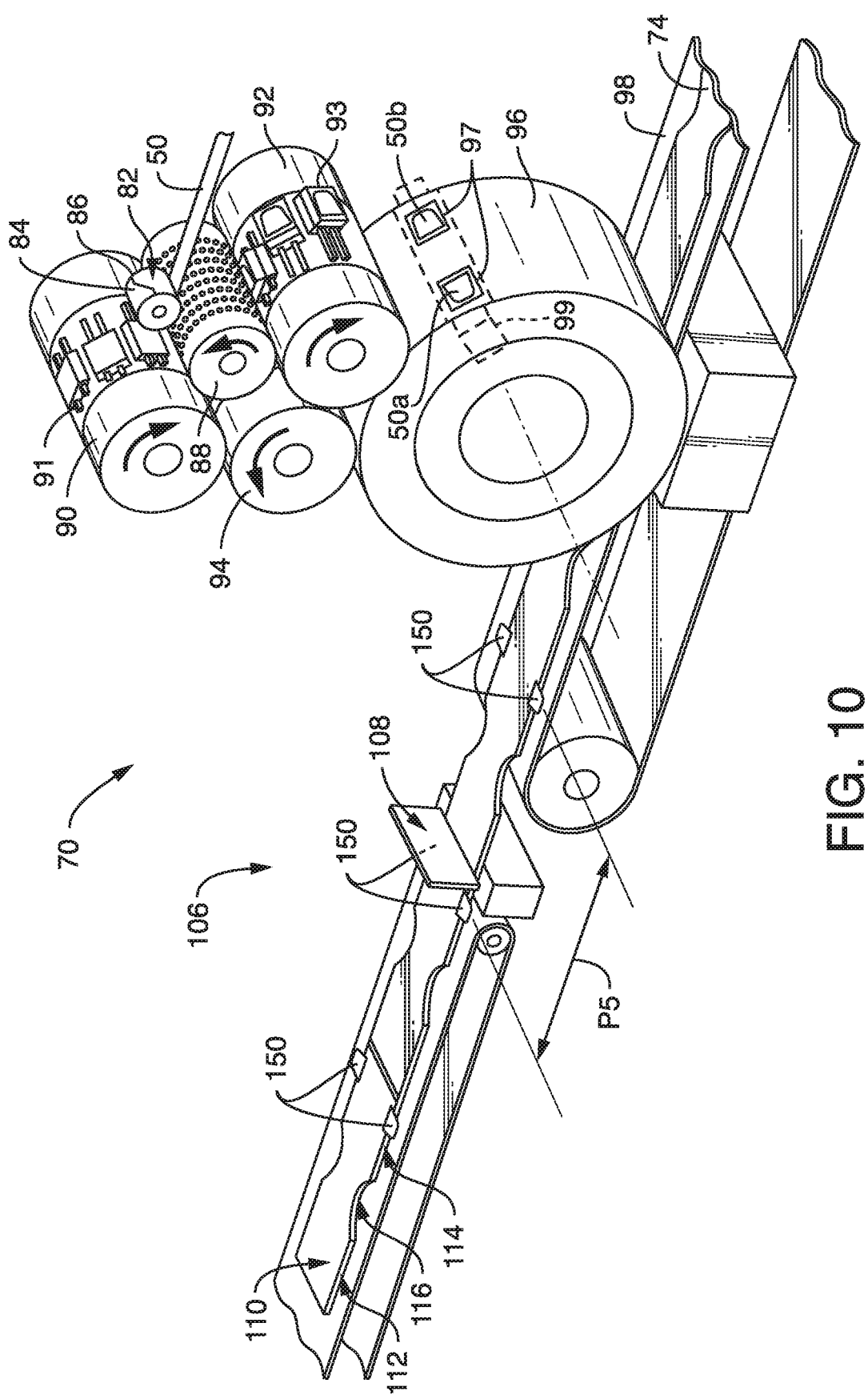
FIG. 10 is a perspective view of an ear cut-and-place module and a cut-off module of the method of FIG. 1
Figure 11:
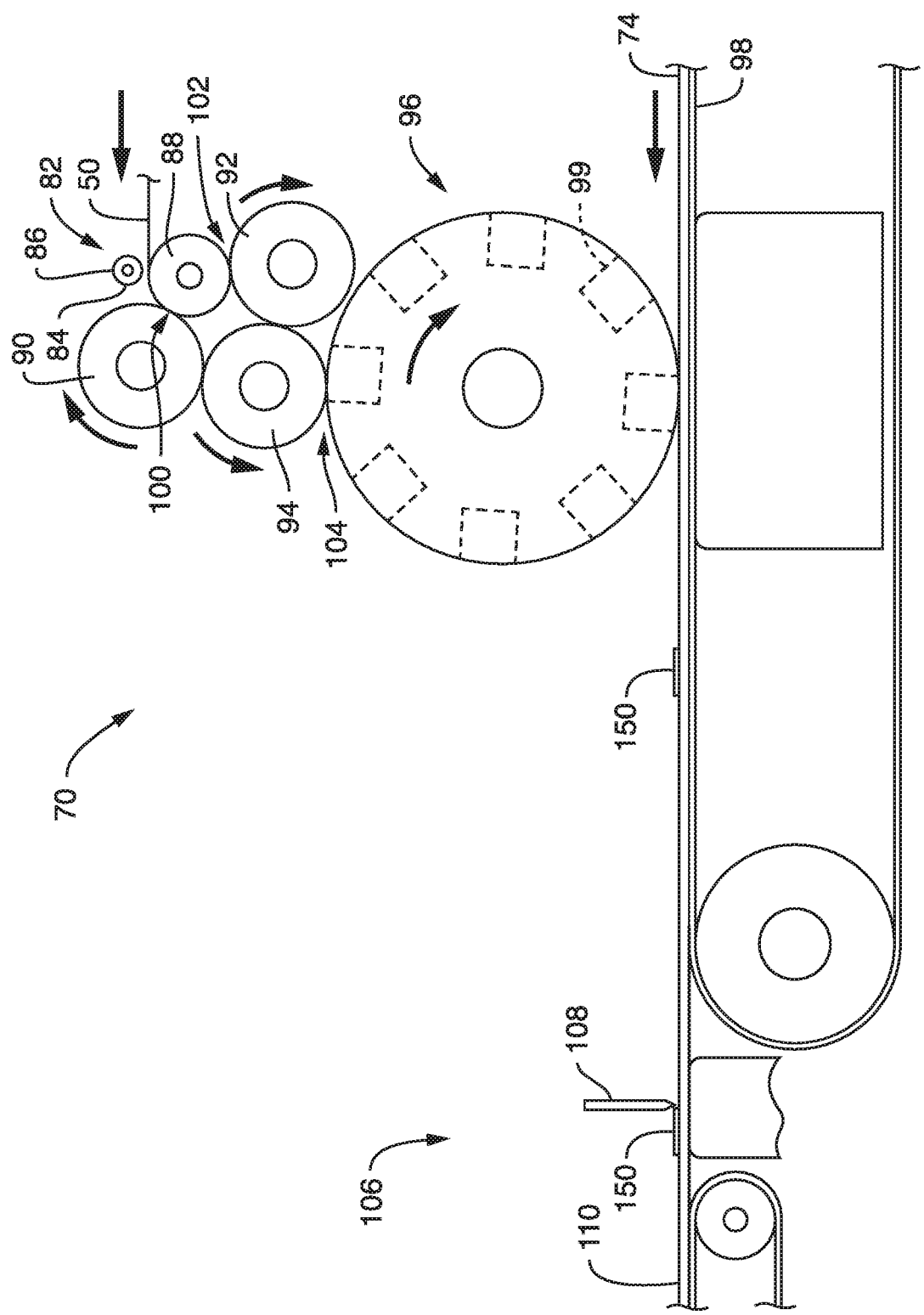
FIG. 11 is a side view of the ear cut-and-place module and the cut-off module of FIG. 10.
Figure 13:
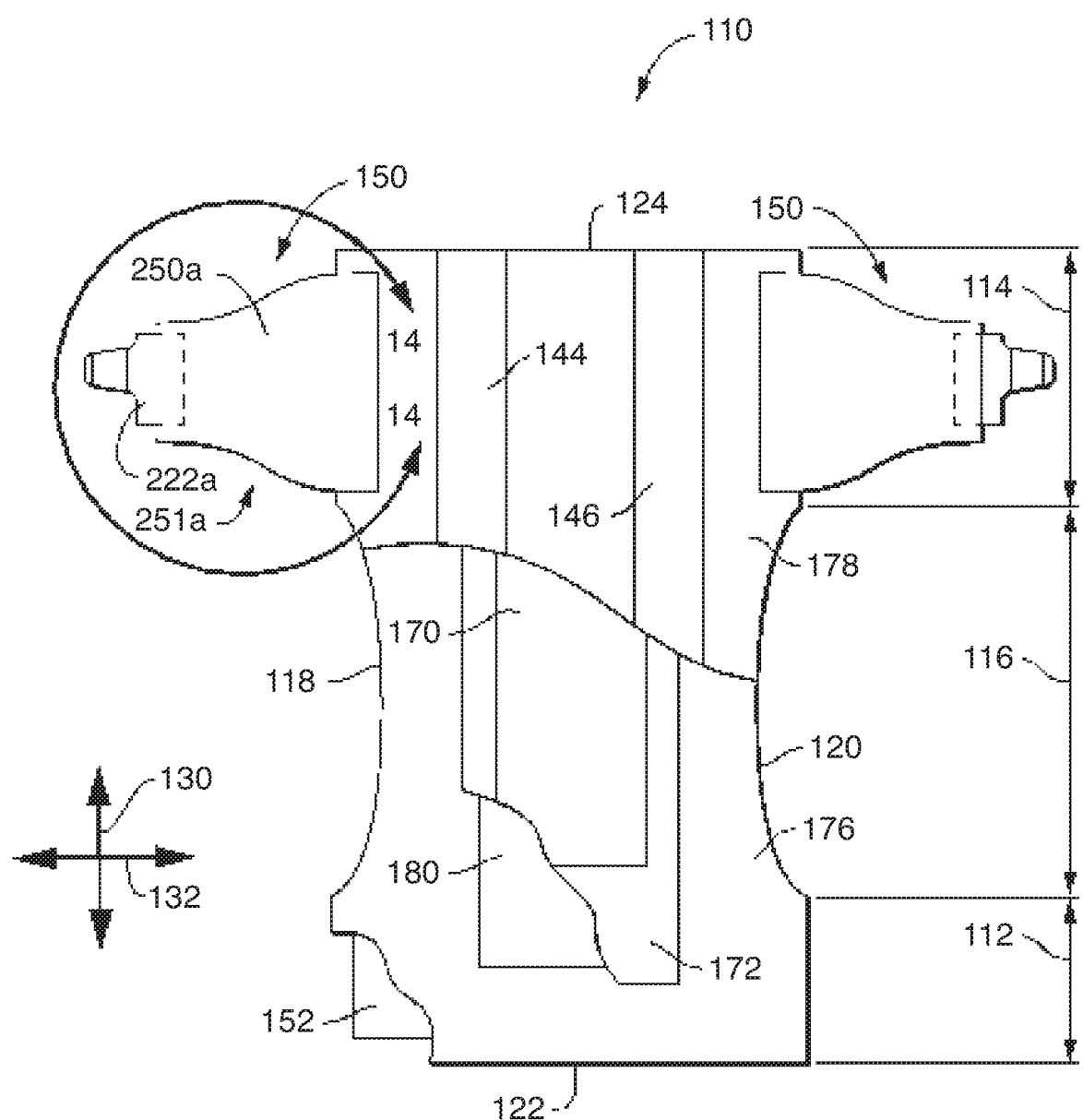
FIG. 13 is a top plan view of an exemplary absorbent article manufactured by the method of FIG. 1 in an unfastened, stretched, and laid flat condition with the body facing surface of the absorbent article which contacts the wearer facing the viewer, portions of the absorbent article being cut away for clarity of illustration.

The ear cut-and-place module 70 can cut the web of ear panel material 50 to form individual ear panels as shown in FIG. 9A or 9B and couple the ear panels to an absorbent assembly 72 (as shown in FIGS. 10 and 11) to form at least a portion of a fastening system of the absorbent article 110. Each ear panel in combination with its associated ear tab can form an ear for the absorbent article 110. For example, FIG. 9A illustrates ears 51a (ear panel 50a and ear tab 24c), 51b, 51c, and 51d and FIG. 9B provides ears 151a (ear panel 150a and ear tab 24c), 151b, 151c, and 151d. In some embodiments, the absorbent assembly 72 of the absorbent article can be provided as a web 74 and can include an outer cover 76, a bodyside liner 78, and an absorbent body 80 disposed between the outer cover 76 and the bodyside liner 78 (as best shown in FIG. 13). The outer cover 76 can be a liquid impermeable material and the bodyside liner 78 can be a liquid permeable material as known by those of ordinary skill in the art. The absorbent body 80 can include absorbent material such as fluff and/or superabsorbent material as is known by those of ordinary skill in the art. The ear cut-and-place module 70 can couple the ear panels to various components of the absorbent assembly 72 as is known by those of ordinary skill in the art, such as the outer cover 76 or the bodyside liner 78.

The functions of the ear cut-and-place module 70 can be performed by various equipment available to those of ordinary skill in the art. One sample piece of equipment capable of performing the functions of the ear cut-and-place module 70 that will be described herein can be purchased from GDM S.P.A., of Bologna, Italy and is illustrated in FIGS. 10-12D. However, it is to be noted that the ear cut-and-place module 70 of method 10 is not limited to the specific processes or equipment of this exemplary equipment described herein, and rather, is intended to encompass any equipment or process capable of performing the general functions of the ear cut-and-place module 70 of cutting individual ear panels from the web of ear panel material 50 and coupling the individual ear panels to the absorbent assembly 72. As another example, another sample piece of equipment capable of performing the functions of the ear cut-and-place module 70 could be the equipment described in U.S. Pat. No. 7,871,400, issued to Sablone et al., the entirety of which is incorporated herein by reference as if set forth in its entirety.

The exemplary ear cut-and-place module 70 as illustrated in FIGS. 10-12D will now be described. As shown in FIG. 10, the ear cut-and-place module 70 can include a cutting device 82 that is capable of cutting the web of ear panel material 50 into individual ear panels, such as the ear panels 50a, 50b, 50c, and 50d shown in FIG. 9A or the ear panel 150a, 150b, 150c, and 150d shown in FIG. 9B. The cutting device 82 can include a cutting roller 84 having opposed blades 86 and a lower roller 88 that is configured to convey individual ear panels that are cut from the web of ear panel material 50. The lower roller 88 can include vacuum holes as shown in FIG. 10 and can be connected to a source of vacuum.

The ear cut-and-place module 70 can also include two single shifter rollers 90, 92, a double shifter roller 94, and an accelerator roller 96. The single shifter rollers 90, 92 rotate clockwise and are at a tangent to a double shifter roller 94. The double shifter roller 94 rotates counter-clockwise and is at a tangent to the accelerator roller 96. The accelerator roller 96 rotates clockwise and is at a tangent with respect to a conveyor 98 transporting the absorbent assembly web 74.

As the web of ear panel material 50 is cut by the blades 86 on the cutting roller 84, the ear panels (e.g., 50a and 50b or 150a and 150b) that can be configured such that adjacent ear panels are generally angled in opposite directions to one another as shown in FIGS. 9A and 9B. The ear panels (e.g., 50a and 50b or 150a and 150b) can be cut by the cutting roller 84 such that no waste is formed from the web of ear panel material 50. In some embodiments, the cutting roller 84 can be configured such that the web of ear panel material 50 is cut to form ear panels that are trapezoidal in shape, such as ear panels 50a, 50b, 50c, 50d shown in FIG. 9A. In other embodiments, the cutting roller 84 can be configured such that the web of ear panel material 50 is cut to form ear panels that include at least one non-linear edge, or at least two non-linear edges, such as ear panels 150a, 150b, 150c, 150d shown in FIG. 9B.

For further discussion of method 10 as depicted in FIGS. 10-12D, the disclosure will refer to the ear panels 50a and 50b processing through the ear cut-and-place module 70, however, because the ear panel 50a is coupled to ear tab 24c to form ear 51a and the ear panel 50b is coupled to ear tab 22d to form ear 51b, reference to ear panels 50a and 50b encompasses ears 51a and 51b. While being cut by the cutting roller 84, the ear panels 50a and 50b are held and transferred by the lower roller 88 rotating in a counter-clockwise direction. From the lower roller 88, ear panel 50a is transferred to single shifter roller 90 at a transition position 100 and ear panel 50b is transferred to a single shifter roller 92 at a transition position 102, as shown in FIGS. 11, 12A, and 12B. The single shifter rollers 90, 92 rotate in a clockwise direction. The single shifter roller 90 includes a plurality of blocks 91 and the single shifter roller 92 includes a plurality of blocks 93, with each of the plurality of blocks 91, 93 on each single shifter roller 90, 92 being circumferentially separated by a distance equal to the pitch P4 between ear panels of the same orientation (e.g., the distance between ear panels 50a and 50c as shown in FIG. 9A). Each block 91, 93 is configured to receive and retain an ear panel (e.g., ear panels 50a and 50b, respectively) and slide in a direction parallel to the axes of the single shifter rollers 90, 92. As shown in FIGS. 10, 12A, and 12B, the blocks 91 on single shifter roller 90 are configured to slide to the left and the blocks 93 on single shifter roller 92 are configured to slide to the right.

Figure 12A:
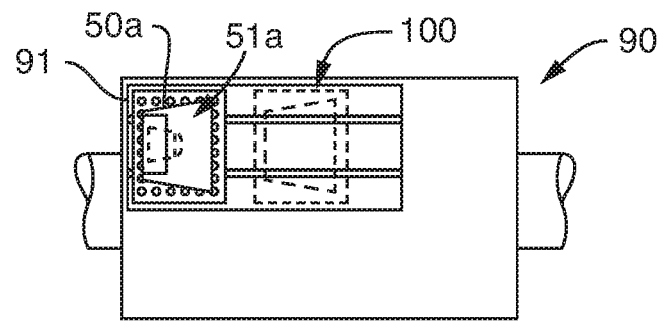
FIG. 12A is a front view of a first single shifter roller of the ear cut-and-place module of FIGS. 10 and 11.
Figure 12B:
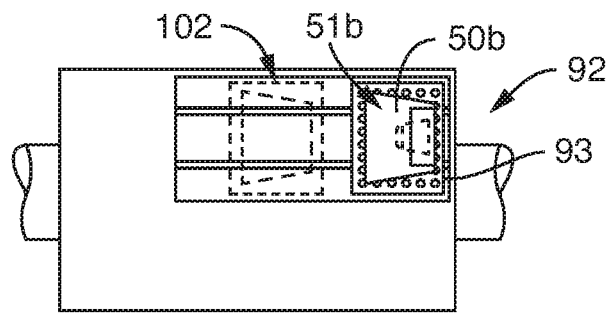
FIG. 12B is a front view of a second single shifter roller of the ear cut-and-place module of FIGS. 10 and 11.
Figure 12C:
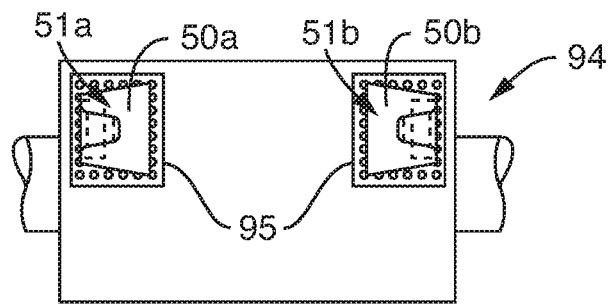
FIG. 12C is a top view of a double shifter roller of the ear cut-and-place module of FIGS. 10 and 11.

As shown in FIGS. 10 and 12C, the double shifter roller 94 rotates in a counter-clockwise direction and includes axially aligned pairs of blocks 95 located near the ends of the double shifter roller 94. During its rotation, double shifter roller 94 receives an ear panel 50a from single shifter roller 90 and an ear panel 50b from single shifter roller 92. The pairs of blocks 95 are configured to receive and retain a pair of ear panels (e.g., ear panels 50a and 50b) and are circumferentially separated from adjacent pairs of blocks 95 by a distance equal to the pitch P4.

Figure 12D:
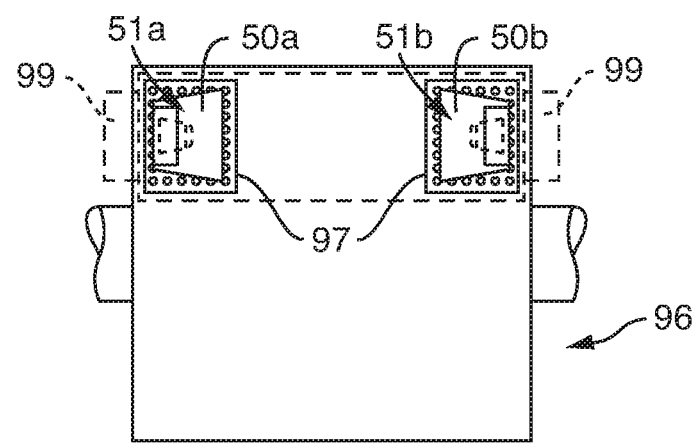
FIG. 12D is a front view of an accelerator roller of the ear cut-and-place module of FIGS. 10 and 11.

The accelerator roller 96 rotates in a clock-wise direction and includes axially aligned pairs of blocks 97 located near the ends of the accelerator roller 96. The pairs of blocks 97 are configured to receive pairs of ear panels (e.g., ear panels 50a and 50b) carried on pairs of blocks 95 on the double shifter roller 94 at a transition position 104, as shown in FIGS. 10, 11, and 12D. Each pair of blocks 97 are mounted on a radial rod 99 that can oscillate during rotation of the accelerator roller 96 on an axis parallel to the longitudinal axis of the accelerator roller 96. Thus, pairs of ear panels (e.g., ear panels 50a and 50b) travel at the tangential velocity of double shifter roller 94 while on blocks 95, but at the transfer to the accelerator roller 96 at transition position 104, pairs of ears (e.g., ear panels 50a and 50b) have the tangential velocity of the accelerator roller 96, which can be configured to be equal to the speed of the web of the absorbent assembly 74. The circumferential spacing of the pairs of the blocks 97 on the accelerator roller 96 is equal to the pitch P5 of pairs of ears 150 on the absorbent assembly web 74. The pairs of blocks 97 on the accelerator 96 can couple the pairs of ear panels (e.g., ear panels 50a and 50b) to the web of the absorbent assembly 74 at the point where the accelerator roller 96 is tangent to the conveyor 98, as shown in FIGS. 10 and 11. As a result, the accelerator 96 can couple pairs of ears (e.g., ears 51a and 51b) to the absorbent assembly 74 to form at least a portion of a fastening system.

Method 10 can also include a cut-off module 106, as illustrated in FIGS. 1, 10, and 11. The cut-off module 106 can include a cut-off knife 108 that can sever the web of the absorbent assembly 74 to form individual absorbent articles 110, as shown in FIGS. 10 and 11.

As illustrated in FIG. 13, the absorbent article 110 can include a front waist region 112, a rear waist region 114, and a crotch region 116 disposed between the front waist region 112 and the rear waist region 114 and interconnecting the front and rear waist regions, 112, 114, respectively. The absorbent article 110 has a pair of longitudinal side edges, 118, 120, and a pair of opposite waist edges, respectively designated front waist edge 122 and rear waist edge 124. The front waist region 112 can be contiguous with the front waist edge 122 and the rear waist region 114 can be contiguous with the rear waist edge 124. The longitudinal side edges 118, 120 can extend from the front waist edge 122 to the rear waist edge 124.

The front waist region 112 can include the portion of the absorbent article 10 that, when worn, is positioned at least in part on the front of the wearer while the rear waist region 114 can include the portion of the absorbent article 110 that, when worn, is positioned at least in part on the back of the wearer. The crotch region 116 of the absorbent article 10 can include the portion of the absorbent article 110, that, when worn, is positioned between the legs of the wearer and can partially cover the lower torso of the wearer. The waist edges, 122 and 124, of the absorbent article 10 are configured to encircle the waist of the wearer. Portions of the longitudinal side edges, 118 and 120, in the crotch region 116 can generally define leg openings when the absorbent article 110 is worn.

The absorbent article 110 can include an absorbent assembly 172 including an outer cover 176 and a bodyside liner 178 and an absorbent body 180 disposed between the outer cover 176 and the bodyside liner 178. In an embodiment, the bodyside liner 178 can be bonded to the outer cover 176 in a superposed relation by any suitable means such as, but not limited to, adhesives, ultrasonic bonds, thermal bonds, pressure bonds, or other conventional techniques. The outer cover 176 can define a length in a longitudinal direction 130, and a width in the lateral direction 132, which, in the illustrated embodiment, can coincide with the length and width of the absorbent article 110. The absorbent article 110 can also include an acquisition layer 170 and a fluid transfer layer 172. The fluid transfer layer 172 can at least partially wrap the absorbent body 180.

The absorbent article 110 can be configured to contain and/or absorb liquid, solid, and semi-solid body exudates discharged from the wearer. For example, laterally spaced containment flaps, 144 and 146, can be configured to provide a barrier to the lateral flow of body exudates. Each containment flap 144, 146 can include elastic members (not shown) as is known in the art. The containment flaps, 144 and 146, can be located laterally inward from the longitudinal side edges, 118, 120 of the absorbent article 110, and can extend longitudinally along the entire length of absorbent article 110 or can extend partially along the length of the absorbent article 110. To further enhance containment and/or absorption of body exudates, the absorbent article 10 can suitably include front and/or rear waist elastic members (not shown).

In an embodiment, the absorbent article 110 can include a fastening system. In one embodiment, the fastening system can include a pair of rear fasteners 150 and one or more front fasteners 152. Portions of the fastening system may be included in the front waist region 112, back waist region 114, or both. The fastening system can be configured to secure the absorbent article 10 about the waist of the wearer and maintain the absorbent article 110 in place during use. In an embodiment, the front fastener 152 can include a landing zone material that forms a loop material, such as a spunbond material embossed to form a point-unbonded material (PUB). In an embodiment, the rear fasteners 150 can include one or more materials coupled together to form an ear manufactured by method 10 discussed above.

Figure 14A:
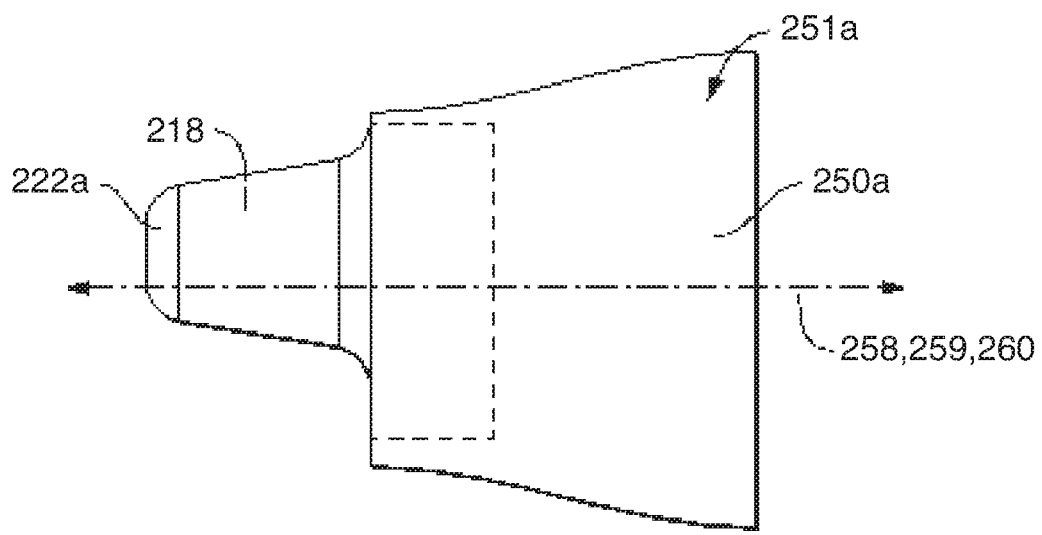
FIG. 14A is a detailed view of an ear taken along line 14-14 from FIG. 13.

For example, FIG. 14A provides a detailed view of the left rear fastener 150 shown in FIG. 13. FIG. 14A illustrates that one of the rear fasteners 150 can be an ear 251a that is asymmetric about the latitudinal axis 260 of the ear 251a. The ear 251a can include an ear panel 250a and an ear tab 222a. The ear panel 250a can include two non-linear sides. The ear tab 222a can include hook material 218 and can be asymmetric about a latitudinal axis 258 of the ear tab 222a, similar to the ear tabs 122a and 122b shown in FIG. 6B and described above. The ear tab 222a can be coupled to the ear panel 250a and the ear panel 250a can be cut such that the latitudinal axis 258 of the ear tab 222a is co-linear with the latitudinal axis 259 of the ear panel 250a. The right rear fastener 150 from FIG. 13 can be constructed in a similar manner as ear 251a, or in a different manner than the ear 251a.

Figure 14B:
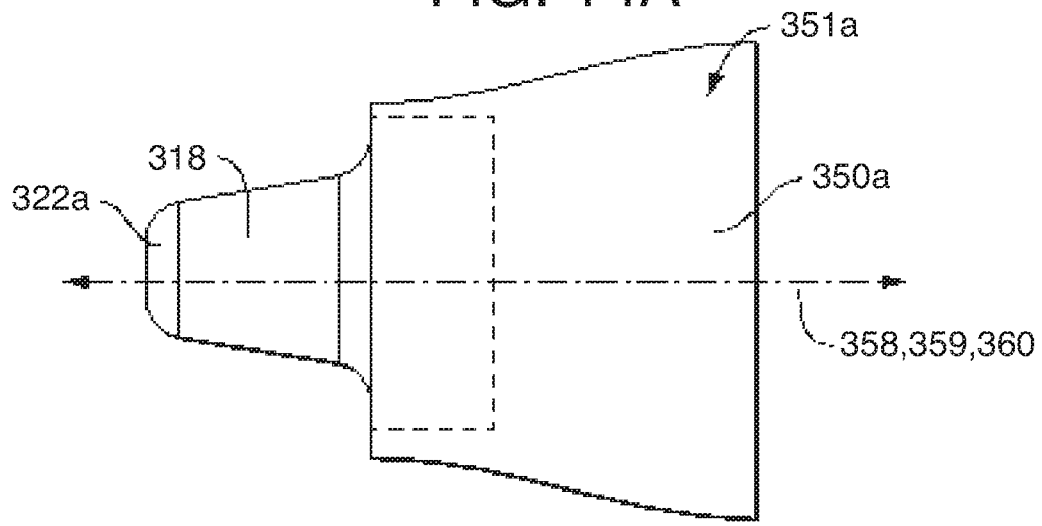
FIG. 14B is a detailed view similar to FIG. 14A, but showing an alternative ear configuration.
Figure 14C:
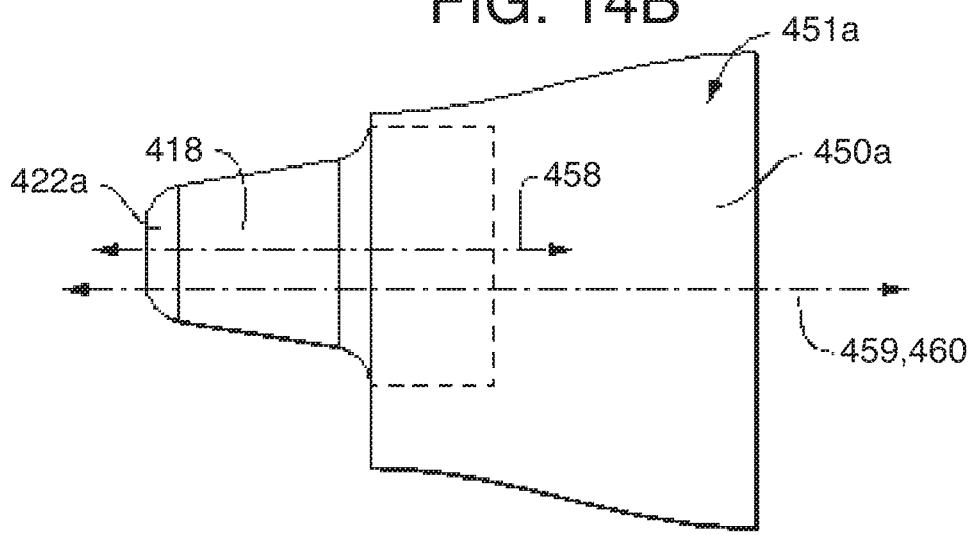
FIG. 14C is a detailed view similar to FIG. 14A, but showing an alternative ear configuration.

FIGS. 14B and 14C provide detailed views of alternative embodiments of ears 351a and 451a that can be manufactured using method 10. FIG. 14B provides a detailed view of ear 351a that is symmetric about the latitudinal axis 360 of the ear 351a. The ear 351a can include an ear panel 350a and ear tab 322a. The ear tab 322a can include hook material 118 and can be symmetric about a latitudinal axis 358 of the ear tab 322a, similar to the ear tabs 22a and 22b shown in FIG. 6A and described above. The ear tab 322a can be coupled to the ear panel 350a and the ear panel 350a can be cut such that the latitudinal axis 358 of the ear tab 322a is co-linear with the latitudinal axis 359 of the ear panel 350a.

The ear 451a of FIG. 14C is asymmetric about the latitudinal axis 460 of the ear 451a. The ear 451a can include an ear panel 450a and an ear tab 422a. The ear tab 422a can include hook material 118 and can be symmetric about a latitudinal axis 458 of the ear tab 422a, similar to the ear tabs 22a and 22b shown in FIG. 6A and described above. The ear tab 422a can be coupled to the ear panel 450a and the ear panel 450a can be cut such that the latitudinal axis 458 of the ear tab 422a is not co-linear with the latitudinal axis 459 of the ear panel 450.

A benefit of the method 10 described herein related to the cutting of registered ear tabs (either symmetric or asymmetric) includes the ability to produce asymmetric ears. Asymmetric ears, such as ear 251a (FIGS. 13 and 14A) and ear 451a (FIG. 14C), can provide improved fastening and fit characteristics on the wearer. As discussed herein, the asymmetric ears can be produced with asymmetric ear tabs, such as ear tab 222a (FIGS. 13 and 14A), or with symmetric ear tabs (FIG. 14C). In these embodiments, the fastening component 118 can provide force characteristics that are not co-linear with the latitudinal axis of the ear panel. For example, the asymmetric ear tab 222a of FIGS. 13 and 14A and the symmetric ear tab 422a each provide for a majority of the fastening component 118 being above the latitudinal axis 260, 460 of the ear 251a, 451a, respectively. As a result, the force of the fastening component 118 in each ear 251a, 451a can be located closer to the front waist edge 122 when the fastening component 118 is engaged with fastening component 152 of the absorbent article. Such a fit can provide improved fit about the waist of a wearer.

Figure 15:
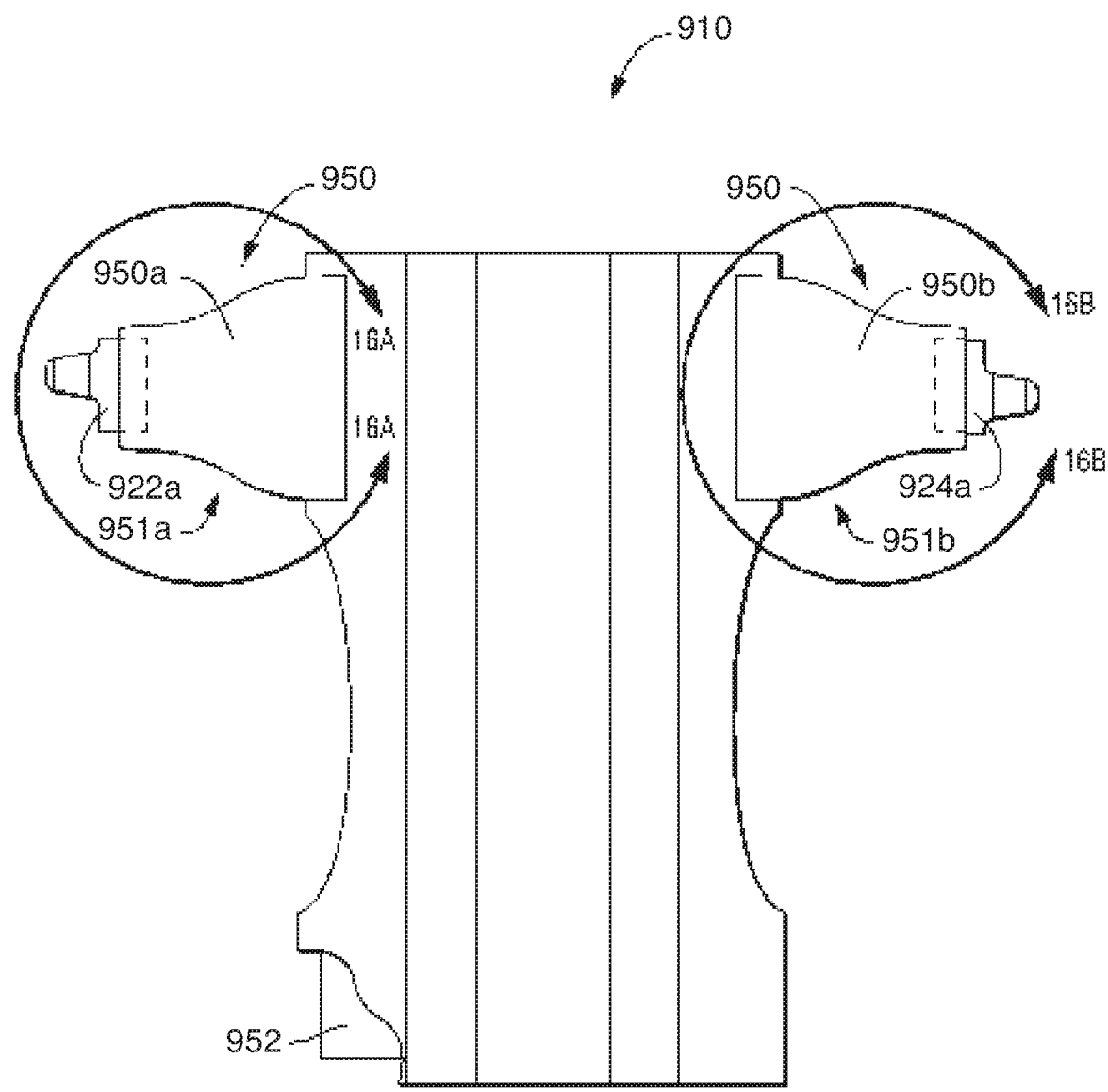
FIG. 15 is a top plan view of another exemplary absorbent article manufactured by the method of FIG. 1 in an unfastened, stretched, and laid flat condition with the body facing surface of the absorbent article which contacts the wearer facing the viewer, portions of the absorbent article being cut away for clarity of illustration.
Figure 16A:
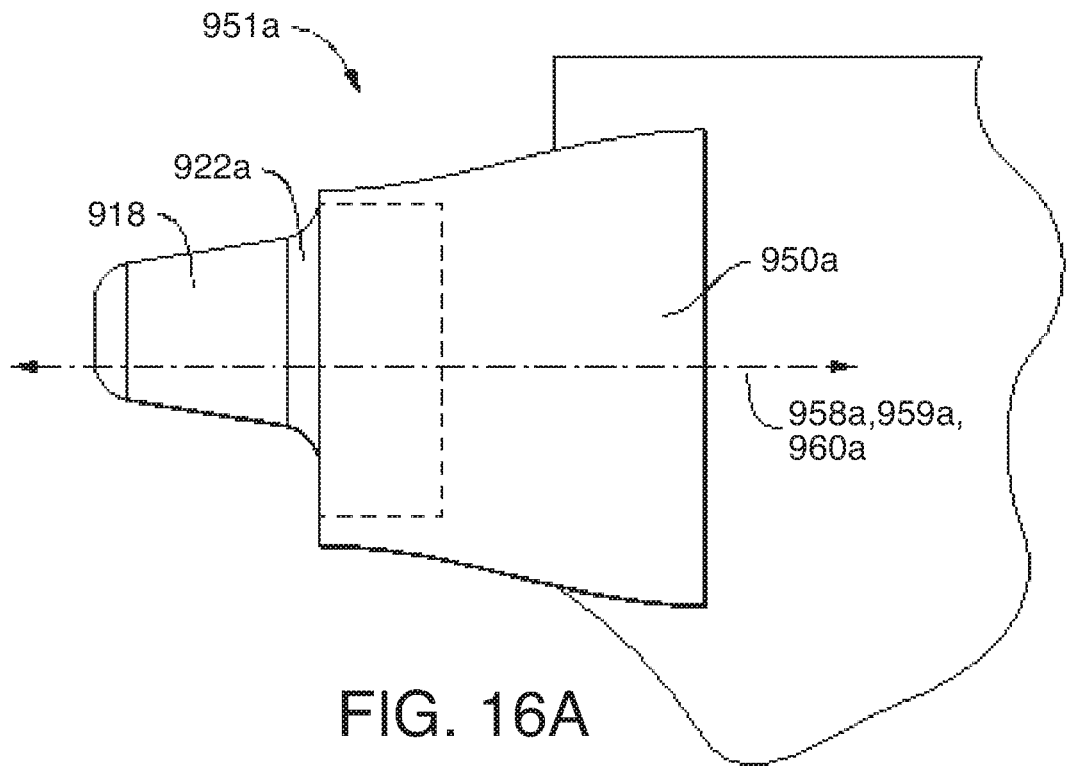
FIG. 16A is a detailed view taken along line 16A-16A from FIG. 15.
Figure 16B:
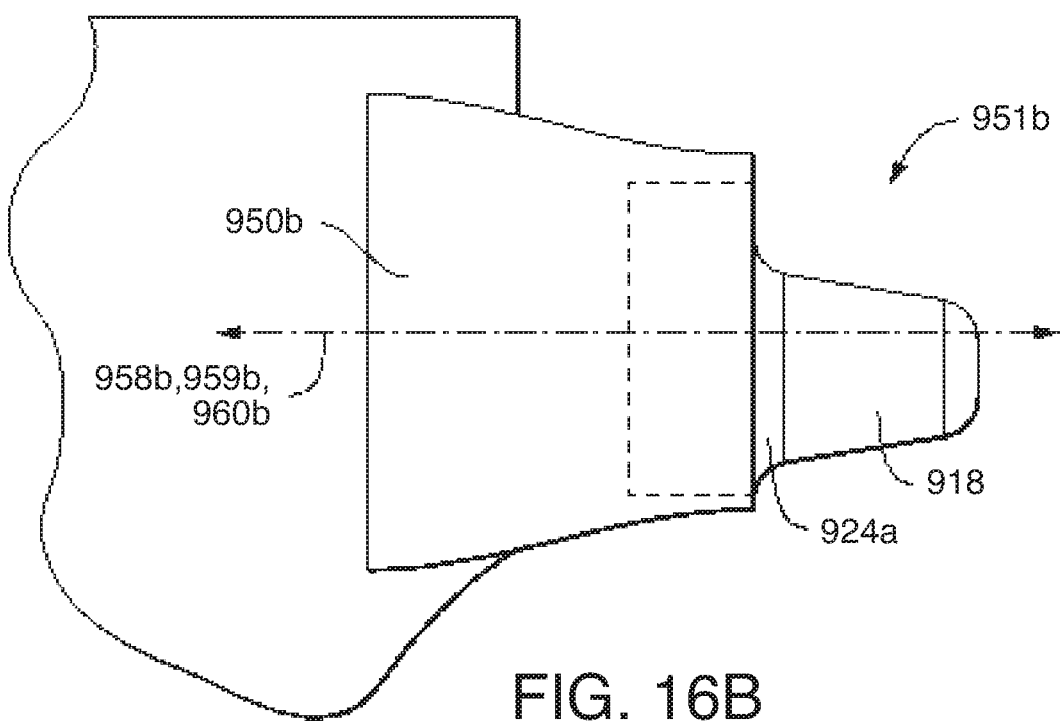
FIG. 16B is a detailed view taken along line 16B-16B from FIG. 15.
Figure 17:
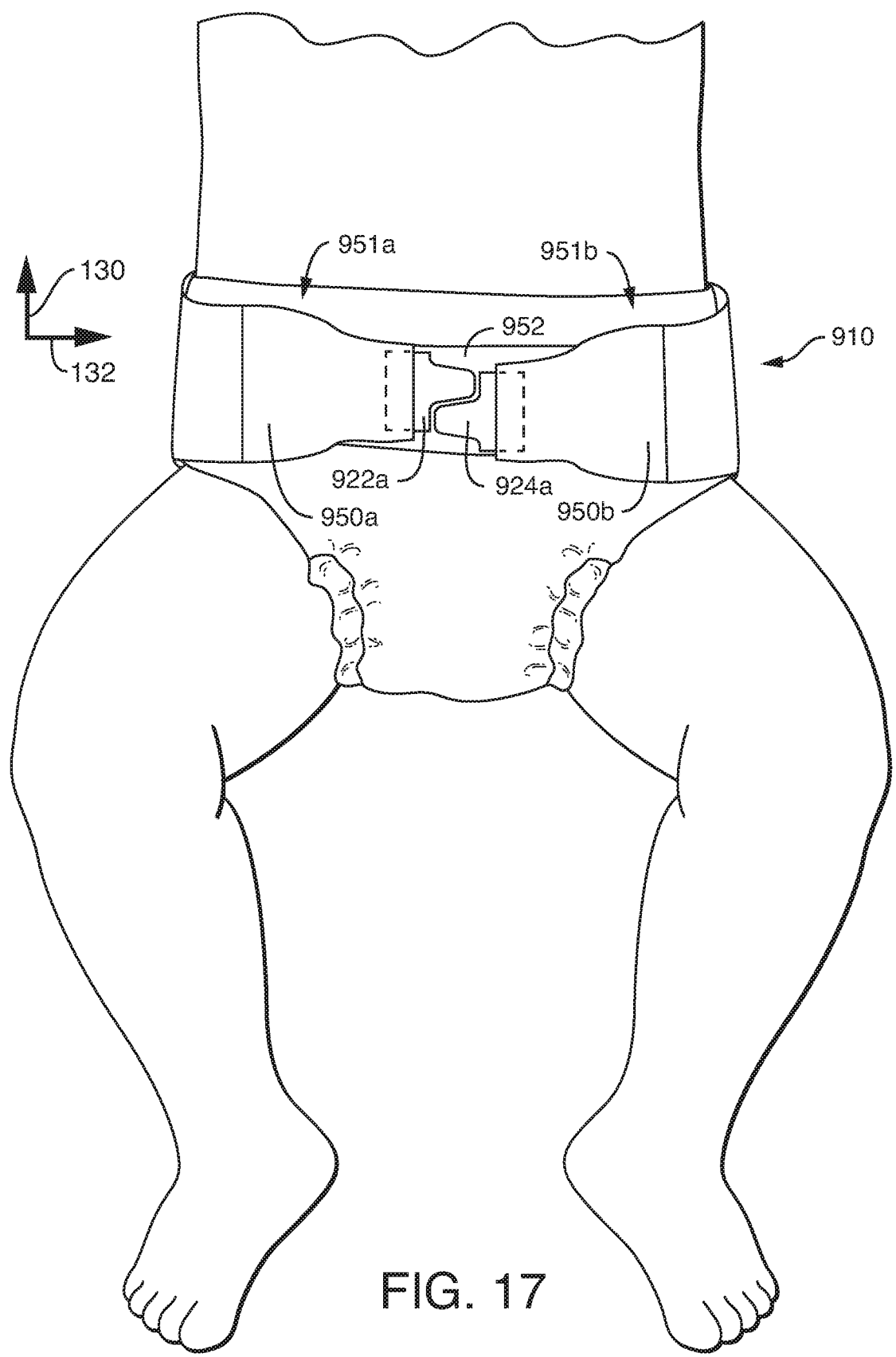
FIG. 17 is a front perspective view of the absorbent article of FIG. 15 fastened about the waist and legs of a wearer.

In another embodiment depicted in FIGS. 15-17, the method 10 can provide an absorbent article 910 having rear fasteners 950 that differ from one another. Specifically, as discussed above with respect to FIG. 6E, an absorbent article 910 can be manufactured according to method 10 in which a left rear ear 951a can include an ear tab 922a that is configured differently than the ear tab 924a on the right rear ear 951b, with the ear tabs 922a, 924b being cut from the first and second webs of ear tab material 22, 24 (such as shown in FIG. 6E). The absorbent article 910 can include a front fastener 952 that can include a landing zone material that forms a loop material. Although absorbent article 910 can be manufactured by method 10 discussed above, it may be manufactured using other methods as well.

As shown in FIG. 16A, the left ear 951a can be asymmetric about the latitudinal axis 960a of the left ear 951a. The ear 951a can include an ear panel 950a and an ear tab 922a. The ear tab 922a can include hook material 918 and can be asymmetric about a latitudinal axis 958a of the ear tab 922a such that a majority of the hook material 918 is above the latitudinal axis 960a of the left ear 950a, as shown in FIG. 16A. The ear tab 922a can be coupled to the ear panel 950a and the ear panel 950a can be cut such that the latitudinal axis 958a of the ear tab 922a is co-linear with the latitudinal axis 959a of the ear panel 950a.

As shown in FIG. 16B, the right ear 951b can be asymmetric about the latitudinal axis 960b of the right ear 951b. The ear 951b can include an ear panel 950b and an ear tab 924a. The ear tab 924a can include hook material 918 and can be asymmetric about a latitudinal axis 958b of the ear tab 924a such that a majority of the hook material 918 is below the latitudinal axis 960b of the right ear 950b, as shown in FIG. 16B. The ear tab 924a can be coupled to the ear panel 950b and the ear panel 950b can be cut such that the latitudinal axis 958b of the ear tab 924a is co-linear with the latitudinal axis 959b of the ear panel 950b.

Referring now to FIG. 17, the absorbent article 910 can be fastened about the waist and legs of a wearer. The configuration of the left and right rear ears 951a, 951b as shown in FIG. 17 provides the benefit of that when the article 910 is fastened, the ear tab 922a on the left rear ear 951a can at least partially overlap with the ear tab 924a on the right rear ear 951b in a cross-direction 132 without the ear tabs 922a, 924a being fastened one on top of the other. The difference between the configurations of the ear tabs 922a, 924b in absorbent article 910 creates a variation of the hook material 918 in the longitudinal direction 130 between the left and right ears 951a and 951b that allow this overlap in the cross-direction 132 without fastening on top of each other. Specifically, the left rear ear 951a has a majority of the hook material 918 above the latitudinal axis 960a of the left rear ear 951 (see FIG. 16A), but the right rear ear 951b has a majority of the hook material 918 below the latitudinal axis 960b of the right rear ear 951b (see FIG. 16B). This offset in the hook material 918 between the left and right ears 951a and 951b in the longitudinal direction 130 allows the same or substantially the same fit of the ear panels 950a, 950b around the wearer's waist and legs on the wearer's left and right sides while still providing the hook material 918 of the ear tabs 922a, 924a to engage the front fastener 952 in the circumstance that there must be some overlap of the hook material 918 on the ear tabs 922a, 924a in the cross-direction 132. Engaging the hook material 918 of the ear tabs 922a, 924a with the front fastener 952 can be preferred over engaging the ear tabs 922a, 924a one on top of another when the tabs 922a, 924a overlap in the cross-direction 132. Such an overlap in the cross-direction may be necessary in circumstances where a wearer has a smaller waist circumference than intended for the step size of the absorbent article 910 being applied. As but one example, this circumstance can be experienced with newborn or prematurely born infants. As an additional benefit, in some embodiments, the ear tabs 922a, 924a may form a nested pattern or puzzle-piece type pattern such as that shown in FIG. 17 that can assist the wearer or user in coupling the rear fasteners 950 to the front fastener 952 where such a fit is required. However, in other embodiments, such a nested pattern is not required, and thus, this disclosure is intended to cover those embodiments as well.

It is to be noted that an overlap of hook material on ear tabs from the left rear ear and the right rear ear in the cross-direction 132 can be accomplished with various ears other than the exemplary embodiment shown in FIGS. 15-17. For example, an overlap of hook material on ear tabs in the cross-direction 132 could be provided with left and right asymmetric ears that have ear tabs (either registered or non-registered) that are symmetric with respect to the latitudinal axis of the ear tabs, but in which the difference between the left and right rear ears is the difference in location of the latitudinal axis of the respective ear tabs in the longitudinal direction 130. Specifically, the ear 451a shown in FIG. 14C could provide one ear on an article where the latitudinal axis 458 of the ear tab 422a is above the latitudinal axis 460 of the ear 451a and a corresponding ear could be constructed such that the latitudinal axis of the ear tab is below the latitudinal axis of the ear panel. Such a configuration would provide that a majority of the hook material is above the latitudinal axis of the ear for one ear, but a majority of the hook material is below the latitudinal axis of the corresponding ear, thus providing the offset in hook material in the longitudinal direction 130 as discussed above. While preferred embodiments include registered ear tabs, this benefit can be provided with non-registered ear tabs as well, which are encompassed by this disclosure.

The method 10 described herein including the cutting of registered ear tabs (either symmetric or asymmetric) can provide several advantageous benefits for ears 150 of an absorbent article 110 produced by method 10. For example, the registered ear tabs (e.g., 22a or 122a shown in FIGS. 6A, 6B, 6E, and 13-17) can provide curved edges which reduce the potential for discomfort or irritation of the wearer's skin. Furthermore, the curved edges of the ear tabs can provide an improved aesthetic for the wearer and/or user and can provide a cue to the wearer and/or user of a higher-tiered product.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   an absorbent assembly comprising an outer cover, a bodyside liner, and an absorbent body disposed between the outer cover and the bodyside liner; and
   a fastening system coupled to the absorbent assembly, the fastening system comprising a first rear ear including a first ear tab with a fastening component coupled to the first rear ear and a second rear ear including a second ear tab with a fastening component coupled to the second rear ear, the first rear ear comprising an outboard edge wherein the fastening component of the first ear tab is disposed wholly outboard of the first rear ear outboard edge and the second rear ear comprising an outboard edge wherein the fastening component of the second ear tab is disposed wholly outboard of the second rear ear outboard edge,
   wherein a majority of the fastening component of the first ear tab is above a latitudinal axis of the first rear ear and a majority of the fastening component of the second ear tab is below a latitudinal axis of the second rear ear,
   wherein the first ear tab is asymmetric with respect to a latitudinal axis of the first ear tab and the second ear tab is asymmetric with respect to a latitudinal axis of the second ear tab, and the latitudinal axis of the first ear tab is co-linear with the latitudinal axis of the first rear ear and the latitudinal axis of the second ear tab is co-linear with the latitudinal axis of the second rear ear, and
   wherein the combined first rear ear and first ear tab and the combined second rear ear and second ear tab are asymmetric about a longitudinal axis of the absorbent article.

2. The absorbent article of claim 1, wherein the first ear tab and the second ear tab are configured such that the first ear tab and the second ear tab can nest together when the absorbent article is in a fastened condition and the first ear tab and the second ear tab overlap one another in a cross-direction.

3. The absorbent article of claim 1, wherein the first ear tab and the second ear tab are each configured as a registered ear tab.

4. An absorbent article comprising:
   an absorbent assembly comprising an outer cover, a bodyside liner, and an absorbent body disposed between the outer cover and the bodyside liner; and
   a fastening system coupled to the absorbent assembly, the fastening system comprising a first rear ear including a first ear tab including a fastening component and coupled to an elastic first rear ear panel material and an elastic second rear ear including a second ear tab including a fastening component and coupled to a second rear ear panel material,
   wherein a majority of the fastening component of the first ear tab is above a latitudinal axis of the first rear ear and a majority of the fastening component of the second ear tab is below a latitudinal axis of the second rear ear, and
   wherein the first ear tab comprises a projection portion and the second ear tab comprises a projection portion with the fastening components disposed wholly on the projection portions of the first and second ear tabs, and the first ear tab and the second ear tab coupled to the elastic rear ear panel materials such that the fastening component of the first ear tab extends wholly outboard of an outboard edge of the first rear ear and the fastening component of the second ear tab extends wholly outboard of an outboard edge of the second rear ear, wherein the first ear tab projection portion comprises laterally extending top and bottom edges and the fastening component of the first ear tab extends to each of the laterally extending top and bottom edges and the second ear tab projection portion comprises laterally extending top and bottom edges and the fastening component of the second ear tab extends to each of the laterally extending top and bottom edges of the projection portion, the laterally extending top edge of the first ear tab projection portion being symmetrical to the laterally extending bottom edge of the first ear tab projection portion and the laterally extending top edge of the second ear tab projection portion being symmetrical to the laterally extending bottom edge of the second ear tab projection portion, and wherein the projection portion of the first ear tab comprises an outboard edge and the fastening component does not extend to the outboard edge of the first ear tab and the projection portion of the second ear tab comprises an outboard edge and the fastening component does not extend to the outboard edge of the second ear tab.

5. The absorbent article of claim 4, wherein the first rear ear panel material is symmetric in shape to the second rear ear panel material.

6. The absorbent article of claim 5, wherein the first rear ear and the second rear ear are coupled to the absorbent assembly at a same longitudinal location on the absorbent assembly and to opposite longitudinally extending sides of the absorbent assembly.

7. The absorbent article of claim 6, wherein the first ear tab is asymmetric with respect to a latitudinal axis of the first ear tab and the second ear tab is asymmetric with respect to a latitudinal axis of the second ear tab.

8. The absorbent article of claim 7, wherein the latitudinal axis of the first ear tab is co-linear with the latitudinal axis of the first rear ear, and the latitudinal axis of the second ear tab is co-linear with the latitudinal axis of the second rear ear.

9. The absorbent article of claim 6, wherein the first ear tab and the second ear tab are configured such that the first ear tab and the second ear tab can nest together when the absorbent article is in a fastened condition and the first ear tab and the second ear tab overlap one another in a cross-direction.

10. The absorbent article of claim 6, wherein the first ear tab and the second ear tab are each configured as a registered ear tab.

11. The absorbent article of claim 7, wherein the first ear tab and the second ear tab are configured such that the first ear tab and the second ear tab can nest together when the absorbent article is in a fastened condition and the first ear tab and the second ear tab overlap one another in a cross-direction.

12. The absorbent article of claim 6, wherein the first ear tab is symmetric with respect to a latitudinal axis of the first ear tab and the second ear tab is symmetric with respect to a latitudinal axis of the second ear tab.

13. The absorbent article of claim 12, wherein the latitudinal axis of the first ear tab is spaced from the latitudinal axis of the first rear ear, and the latitudinal axis of the second ear tab is spaced from the latitudinal axis of the second rear ear.

14. The absorbent article of claim 12, wherein the first ear tab and the second ear tab are configured such that the first ear tab and the second ear tab can nest together when the absorbent article is in a fastened condition and the first ear tab and the second ear tab overlap one another in a cross-direction.

15. The absorbent article of claim 1, wherein the first ear tab comprises a projection portion and the second ear tab comprises a projection portion, the projection portion of the first ear tab extending wholly outboard of the first rear ear outboard edge and the projection portion of the second ear tab extending wholly outboard of the second rear ear outboard edge.

16. The absorbent article of claim 15, wherein the first ear tab projection portion comprises laterally extending top and bottom edges and the fastening component extends to each of the laterally extending top and bottom edges of the projection portion of the first ear tab, and wherein the second ear tab projection portion comprises laterally extending top and bottom edges and the fastening component extends to each of the laterally extending top and bottom edges of the projection portion of the second ear tab.

17. The absorbent article of claim 16, wherein the projection portion of the first ear tab comprises an outboard edge and the fastening component does not extend to the outboard edge of the first ear tab, and wherein the projection portion of the second ear tab comprises an outboard edge and the fastening component does not extend to the outboard edge of the second ear tab.

18. The absorbent article of claim 1, wherein the first rear ear comprises an elastomeric material separate from the absorbent assembly and coupled to the absorbent assembly.

* * * * *